(12) United States Patent
Ephrat

(10) Patent No.: US 9,892,475 B1
(45) Date of Patent: Feb. 13, 2018

(54) SYSTEM AND METHOD FOR INTERACTIVE CLINICAL SUPPORT AND COMPLIANCE WITH CLINICAL STANDARDS AND GUIDELINES IN REAL-TIME

(75) Inventor: Eyal Ephrat, New York, NY (US)

(73) Assignee: E&C MEDICAL INTELLIGENCE, INC., New York, NY (US)

(*) Notice: Subject to any disclaimer, the term of this patent is extended or adjusted under 35 U.S.C. 154(b) by 2481 days.

(21) Appl. No.: 11/592,902

(22) Filed: Nov. 3, 2006

(51) Int. Cl.
G06Q 10/00 (2012.01)
G06Q 50/00 (2012.01)
G06Q 50/24 (2012.01)

(52) U.S. Cl.
CPC ............... G06Q 50/24 (2013.01)

(58) Field of Classification Search
USPC .......................... 705/2–3; 600/300
See application file for complete search history.

(56) References Cited

U.S. PATENT DOCUMENTS

| | | |
|---|---|---|
| 4,951,680 A | 8/1990 | Kirk et al. |
| 5,301,680 A | 4/1994 | Rosenberg |
| 5,442,940 A | 8/1995 | Secker et al. |
| 5,494,032 A | 2/1996 | Robinson et al. |
| 5,594,638 A | 1/1997 | Iliff |
| 5,596,993 A | 1/1997 | Oriol et al. |
| 5,609,156 A | 3/1997 | Keith et al. |
| 5,746,212 A | 5/1998 | Rall et al. |

(Continued)

*Primary Examiner* — Robert W Morgan
*Assistant Examiner* — Rajiv J Raj
(74) *Attorney, Agent, or Firm* — Stoel Rives LLP

(57) ABSTRACT

A method and system for assisting clinical staff in providing optimal care in real-time and assisting in compliance with clinical standards and guidelines. The system performs the steps of receiving items of patient data, comparing the received patient data with a set of best practice rules to determine if at least one item of patient data has not been received. The patient data can include patient information, diagnosis, decision, or an action to be taken. The system generates a first notification if an item of patient data has not been received. The first notification is generated based on the comparison of the received patient data with the set of best practice rules. The system displays the first notification, which includes a selectable portion for entering data corresponding to the at least one item of patient data that has not been received. The system upgrades the first notification to be redisplayed again at predetermined time intervals, based on a set of best practice rules, representing the organization's best practices, which determine that such missing patient data is critical for assuring the best clinical care is provided to the patient. The notification continues to be redisplayed until such item of missing patient data is received by the system. After a predetermined time period, based on the patient's clinical situation and the best practice protocols, the system further upgrades the notification to be presented at a central monitor for wider audience notification. After an additional predetermined time period, based on the patient's clinical situation and the best practice protocols, the system further upgrades the notification and mandates the entry of the reasoning why this critically missing patient data is not received. The staff, at that point, must either enter the missing data or provide the reasoning why the data in not entered.

25 Claims, 33 Drawing Sheets

(56) References Cited

U.S. PATENT DOCUMENTS

| | | | |
|---|---|---|---|
| 5,817,035 A | 10/1998 | Sullivan et al. | |
| 5,954,663 A | 9/1999 | Gat et al. | |
| 6,076,065 A | 6/2000 | Clawson | |
| 6,115,624 A | 9/2000 | Lewis et al. | |
| 6,200,279 B1 | 3/2001 | Paltieli | |
| 6,254,537 B1 | 7/2001 | Nguyen | |
| 6,440,089 B1 | 8/2002 | Shine | |
| 6,522,916 B1 | 2/2003 | Kwon | |
| 6,610,012 B2 | 8/2003 | Mault | |
| 6,804,656 B1 | 10/2004 | Rosenfeld et al. | |
| 7,124,031 B1 | 10/2006 | Hoffman et al. | |
| 7,188,151 B2 | 3/2007 | Kumar et al. | |
| 7,195,600 B2 | 3/2007 | Ueda et al. | |
| 7,256,708 B2 | 8/2007 | Rosenfeld et al. | |
| 7,307,543 B2 | 12/2007 | Rosenfeld et al. | |
| 7,315,825 B2 | 1/2008 | Rosenfeld et al. | |
| 7,321,862 B2 | 1/2008 | Rosenfeld et al. | |
| 7,333,850 B2 | 2/2008 | Marossero et al. | |
| 7,337,172 B2 | 2/2008 | Shapiro | |
| 7,395,216 B2 | 7/2008 | Rosenfeld et al. | |
| 7,411,509 B2 | 8/2008 | Rosenfeld et al. | |
| 2002/0196959 A1 | 12/2002 | Gurner | |
| 2003/0050799 A1 | 3/2003 | Jay et al. | |
| 2003/0146942 A1 | 8/2003 | Helgason | |
| 2004/0078219 A1 | 4/2004 | Kaylor et al. | |
| 2004/0082842 A1 | 4/2004 | Lumba et al. | |
| 2004/0100376 A1 | 5/2004 | Lye et al. | |
| 2004/0243015 A1 | 12/2004 | Smith et al. | |
| 2004/0254430 A1 | 12/2004 | Hamilton | |
| 2005/0049509 A1 | 3/2005 | Mansour et al. | |
| 2006/0009697 A1 | 1/2006 | Banet et al. | |
| 2006/0183980 A1 | 8/2006 | Yang | |
| 2006/0189882 A1 | 8/2006 | Thomas | |
| 2006/0218010 A1 | 9/2006 | Michon et al. | |
| 2006/0240495 A1 | 10/2006 | Buhimschi et al. | |
| 2007/0143143 A1* | 6/2007 | Villasenor | G06F 19/327 705/2 |
| 2008/0058614 A1 | 3/2008 | Banet et al. | |
| 2008/0201174 A1* | 8/2008 | Ramasubramanian | G06F 19/3456 705/3 |

\* cited by examiner

Patient Chart

FIG. 3

Admission | Follow up | Orders | Labs | Reports — 171, 175, 177

Demographics
- Linda Johnson, Social Security Number: 8756565, Date of birth: 07/01/1977, 29.2 years old, single, mother of one child. Registered at 15:43 08/27/2006. — 25

Admission Information

Dating / # of Fetuses
- Working gestational age (according to selected LMP) is 38 weeks + 0 days. Last menstrual period = 12/04/2005. Menstrual regularity: regular frequency: 28 days. The patient hadn't been using any contraception. Expected date of delivery: 09/10/2006. — 27

Obstetric History
- Formula: G 3, P 1 0 1 1.
  Gravidity - 3, Parity - 1, Term - 1, Preterm - 0, Induced Abortions - 1, Living Children - 1, Multiple Deliveries- 0, CS - 0.
  G 1: In 2000, birth at 39 weeks. Live born: yes. Birth weight: 2783 g. Fetal sex was male. Apgar: 1 min: 9, 5 min: 10, 10 min: 10. Complicated neonatal course. Neonatal Complications: sepsis caused by GBS. Vaginal delivery (Normal, Spontaneous). — 29

Height and Weight
- Last documented height: 5 feet and 5 inches = 165 cm (15:46 08/27/2006).
- Last documented weight: 150 lbs = 68.2 kg (15:46 08/27/2006). — 31

Chief Complaint

Prenatal Care
- Patient had prenatal care. Patient had an uneventful pregnancy.

Prenatal Labs
- Blood Type (07/01/2006): AB negative.
  Viral serology (07/01/2006): Rubella IgG - immune.
  Hepatitis serology (07/01/2006): HBsAg: negative.
  Bacterial serology (07/01/2006): RPR: nonreactive.
  Vaginal microbiology results (07/01/2006): GBS recto-vaginal: unknown. — 33

Tabs: History | Entry log | Flowsheet — 185

Labels: 23, 24, 300 (Done)

CAM Phase II

The blinking prompts 139 and 140 appear after 10 minutes from SROM

System's Central Monitor

SYSTEM AND METHOD FOR INTERACTIVE CLINICAL SUPPORT AND COMPLIANCE WITH CLINICAL STANDARDS AND GUIDELINES IN REAL-TIME

TECHNICAL FIELD

The present invention generally relates to a patient record system used in a medical treatment facility, and more particularly to a method and system designed to assist the clinical staff in providing the optimal care in real-time and assisting in compliance with clinical standards and guidelines.

BACKGROUND

Recently, medical errors and their associated malpractice crisis have become a growing concern in healthcare, and now more than ever before, clinicians are required to better adhere to practice guidelines and documentation quality. These guidelines require appropriate and timely execution of medical evaluations, diagnoses, actions and decisions, as well as detailed and accurate documentation in the patient's chart.

The appropriate management of the patient's case involves a complex combination of essential information that must be evaluated pertinent to the specific clinical case and appropriately documented in a patient chart, and making the right diagnosis and the right management actions. The clinical situation may change from one moment to the next, based on the passage of time or developments in the patient's condition that require further evaluation of the clinical situation, documentation, diagnosis and decisions on management actions. These steps may include gathering additional data about the patient, performing additional tests or medical procedures on the patient and administering medication to the patient. Additionally, these steps can include the course of treatment scheduled to be performed or other clinical events. However, if a failure occurs along these complex processes, e.g. the appropriate evaluation is not done or not documented, the appropriate diagnosis is not made, the appropriate decisions are not made or the appropriate actions are not taken, each of those failures may lead to a catastrophic clinical error, which may lead to patient injury and malpractice events. The current method of patient management, when the staff is highly exposed to such failures in the real-time setting, is the primary reason for the growing concerns in the healthcare industry leading to a major need for quality control processes and mechanisms in healthcare to assure that a higher quality of practice is provided to the patients.

The present invention is designed to provide solutions to the failures in patient management described above by providing a method and system for assisting in real-time adherence to practice guidelines and essential medical and legal documentation standards. The present system and method presents clinicians, through specific alerts, reminders, suggestions and prompts, with the appropriate real-time case- and situation-specific care options, including the essential pertinent documentation, diagnosis, decisions and actions, and provides full support for best pertinent risk management pathways and documentation. The system also identifies the severity of the nearing failure and is able to escalate, as time passes, clinical reminders, prompts and alerts to avoid the clinical error, thereby serving as a powerful tool for quality assurance and malpractice reduction.

SUMMARY

The present invention relates to a method for assisting in compliance with a clinical standard or guideline, pertinent to the patient's specific clinical situation. The method may include the steps of receiving at least one item of patient clinical data or the passing of a certain amount of time; analyzing the new set of clinical data existing in the system, including the progression of time, against rules representing clinical standards and guidelines; generating a first notification requesting at least one missing item of patient medical data or at least one missing item of clinical action/decision or at least one missing item of clinical diagnosis, the notification generated based on the rules' determination that the new set of data and time requires the staff to provide such missing item; displaying the first notification at a first predetermined time, the first notification including a selectable portion for inputting the missing item or items of patient medical data or the missing item or items of clinical action/decision or the missing item or items of clinical diagnosis; receiving the missing item or items as such; displaying the first notification at a second predetermined time if the missing item or items of patient medical data or the missing item or items of clinical action/decision or the missing item or items of clinical diagnosis are not received by the second predetermined time, that notification including a reminder that the missing item or items have not been completed; continuing such notifications at the second predetermined time intervals until the missing item or items of patient medical data or the missing item or items of clinical action/decision or the missing item or items of clinical diagnosis is received; displaying a second notification at a third predetermined time if the missing item or items of patient medical data or the missing item or items of clinical action/decision or the missing item or items of clinical diagnosis is not received after the third predetermined, the second notification including a reminder that the missing item or items have not been completed; and, displaying a third notification at a fourth predetermined time if the missing item or items of patient medical data or the missing item or items of clinical action/decision or the missing item or items of clinical diagnosis is not received after the fourth predetermined time, the fourth notification including a mandatory portion for inputting the missing item or items or, instead, inputting a reason why the missing item or items has not been completed.

BRIEF DESCRIPTION OF THE DRAWINGS

FIG. 3-16 are screenshots of the patient record system described herein; and

FIG. 17A-18B are flowcharts illustrating the patient record system described herein.

DETAILED DESCRIPTION

Figure 1:
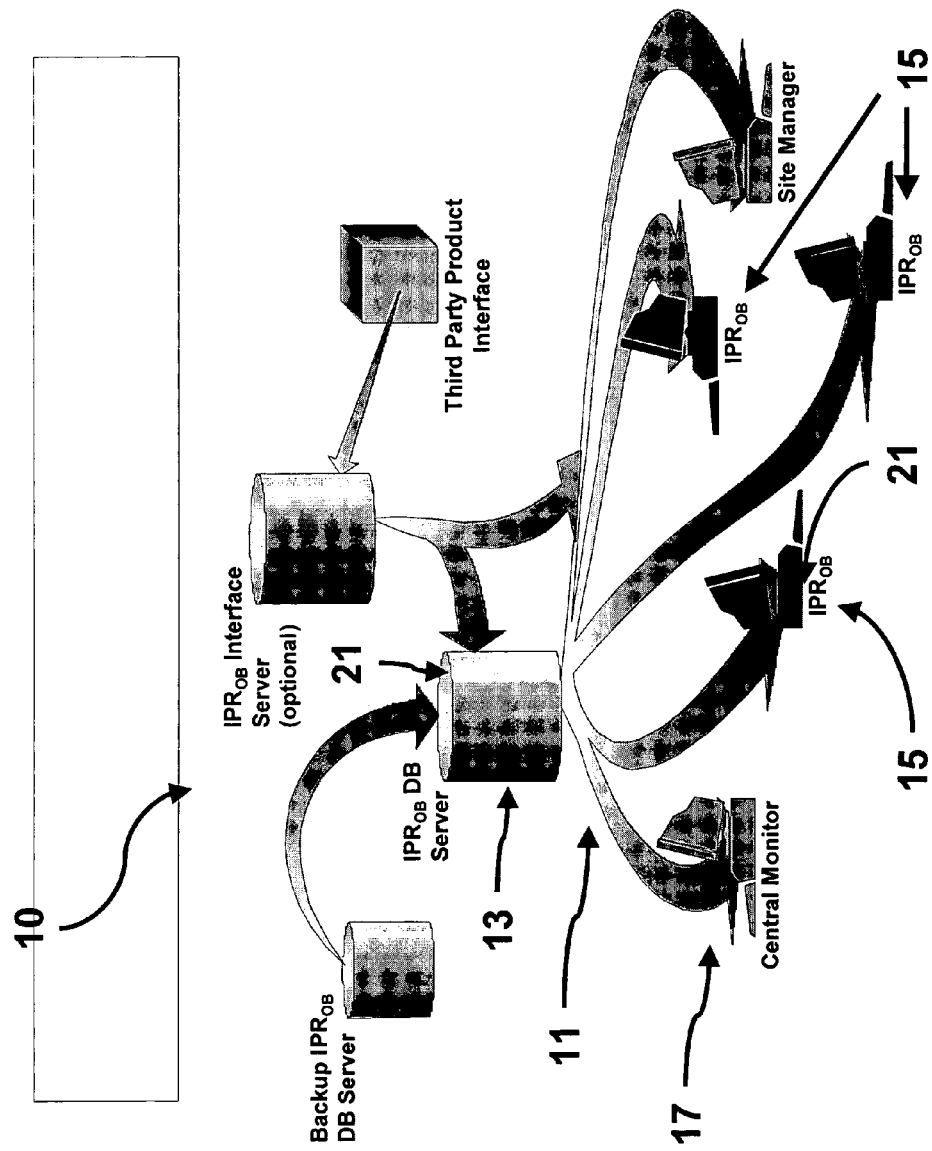
FIG. 1 is a block diagram illustrating a patient record system used in a medical treatment facility.

While this invention is susceptible of embodiments in many different forms, there is shown in the drawings and will herein be described an example of the invention with the understanding that the present disclosure is to be considered as an exemplification of the principles of the invention and is not intended to limit the broad aspect of the invention to the examples illustrated.

FIG. 1 is a block diagram of patient record system 10 used in a medical treatment facility. The patient record system 10 includes a server 13, a plurality of workstations 15, and a central terminal 17, linked by a network 11. Generally, the patient record system 10 is an intelligent patient record system driven by a clinical knowledge-base. The system 10 provides real-time clinical decision support during medical care. For example, in the obstetrics area, the system 10 provides support for prenatal, labor and delivery, and postpartum. The system 10 supports clinicians, through real-time suggestions, prompts, reminders and alerts, in providing the best patient care based on the hospital's clinical standards and guidelines, and supports the staff in avoiding clinical mistakes and generating meticulous documentation. In addition, the system 10 provides reminders, alerts and suggestions of optimal pertinent risk management pathways and documentation.

Figure 2:
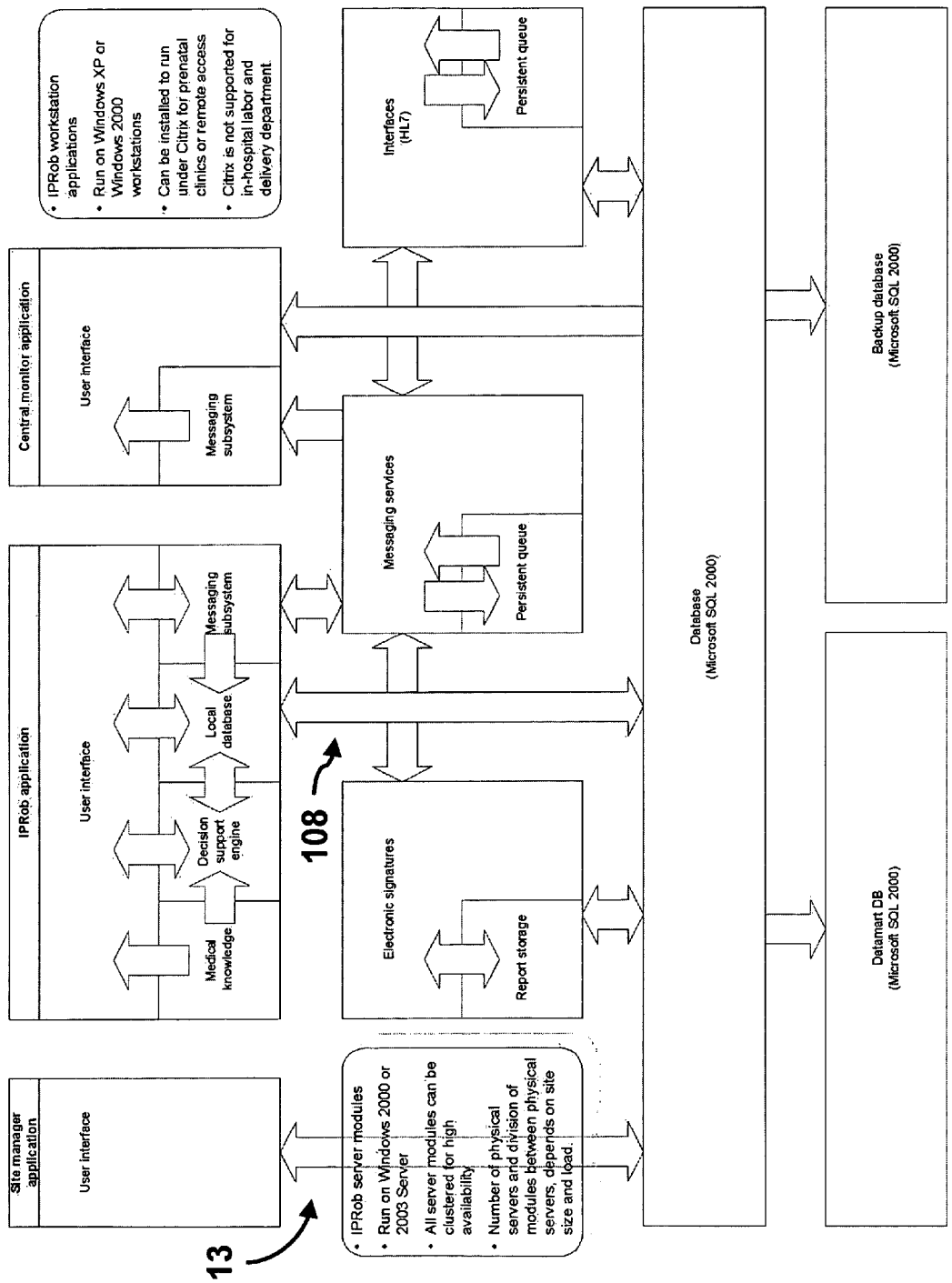
FIG. 2 is a block diagram illustrating a computer in the medical treatment facility of FIG. 1.

FIG. 2 is a schematic diagram of the server 13 having software in the form of an executable computer program. Generally, the computer program is executed by one or more special or general purpose digital computer(s), such as a personal computer (PC; IBM-compatible, or otherwise), personal digital assistant, workstation, minicomputer, or mainframe computer.

Generally, in terms of hardware architecture, the server 13 includes a processor, memory, and one or more input and/or output (I/O) devices (or peripherals) that are communicatively coupled via a local interface 108. The local interface 108 can be, for example, but not limited to, one or more buses or other wired or wireless connections, as is known in the art. The local interface 108 may have additional elements, which are omitted for simplicity, such as controllers, buffers (caches), drivers, repeaters, and receivers, to enable communications. Further, the local interface may include address, control, and/or data connections to enable appropriate communications among the other computer components.

The processor is a hardware device for executing software, particularly software stored in memory. The processor can be any custom made or commercially available processor, a central processing unit (CPU), an auxiliary processor among several processors associated with the server 13, a semiconductor based microprocessor (in the form of a microchip or chip set), a macroprocessor, or generally any device for executing software instructions. Examples of suitable commercially available microprocessors are as follows: a PA-RISC series microprocessor from Hewlett-Packard Company, an 80×86 or Pentium series microprocessor from Intel Corporation, a PowerPC microprocessor from IBM, a Sparc microprocessor from Sun Microsystems, Inc., or a 68xxx series microprocessor from Motorola Corporation.

The memory can include any one or a combination of volatile memory elements (e.g., random access memory (RAM, such as DRAM, SRAM, SDRAM, etc.)) and nonvolatile memory elements (e.g., ROM, hard drive, tape, CDROM, etc.). Moreover, memory may incorporate electronic, magnetic, optical, and/or other types of storage media. The memory can have a distributed architecture where various components are situated remote from one another, but can be accessed by the processor.

The software in memory may include one or more separate programs, each of which comprises an ordered listing of executable instructions for implementing logical functions. The software in the memory of the server 13 includes a medical record computer program with support and compliance capabilities and a suitable operating system (O/S). An examples of suitable commercially available operating systems is Windows operating system available from Microsoft Corporation; The operating system controls the execution of the present computer program.

If the server 13 is a PC or workstation, the software in the memory may further include a basic input output system (BIOS). The BIOS is a set of essential software routines that initialize and test hardware at startup, start the O/S, and support the transfer of data among the hardware devices. The BIOS is stored in ROM so that the BIOS can be executed when the server 13 is activated.

When the server 13 is in operation, the processor is configured to execute software stored within the memory, to communicate data to and from the memory, and to generally control operations of the server 13 pursuant to the software.

The medical record computer program with support and compliance capabilities may reside in, or have portions residing in, any computer such as, but not limited to, the server 13. The medical record computer program with support and compliance capabilities may be a source program, executable program (object code), script, or any other entity comprising a set of instructions to be performed. When a source program, the program needs to be translated via a compiler, assembler, interpreter, or the like, which may or may not be included within the memory, so as to operate properly in connection with the O/S. Furthermore, the medical record computer program with support and compliance capabilities can be written as (a) an object oriented programming language, which has classes of data and methods, or (b) a procedure programming language, which has routines, subroutines, and/or functions, for example, but not limited to, C, C++, Pascal, Basic, Fortran, Cobol, Perl, Java, and Ada. In one embodiment, the medical record computer program with support and compliance capabilities is written in C++. In other embodiments the medical device operating system is created using Power Builder. The I/O devices may include input devices, for example, but not limited to, a keyboard, mouse, scanner, microphone, touch screens, interfaces for various medical devices, bar code readers, stylus, laser readers, radio-frequency device readers, etc. Furthermore, the I/O devices may also include output devices, for example, but not limited to, a printer, bar code printers, displays, etc. Finally, the I/O devices may further include devices that communicate both inputs and outputs, for instance, but not limited to, a modulator/demodulator (modem; for accessing another device, system, or network), a radio frequency (RF) or other transceiver, a telephonic interface, a bridge, a router, etc.

It should be noted that executable computer programs, such as the medical record computer program with support and compliance capabilities can be stored on any computer readable medium for use by or in connection with any computer related system or method. In the context of the invention, a computer-readable medium can be any means that can store, communicate, propagate, or transport the program for use by or in connection with the instruction execution system, apparatus, or device. The computer readable medium can be for example, but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical).

Referring again to FIG. 1, both the server 13 and the workstations 15 may include a knowledgebase 21 (database with machine-formatted knowledge) of best practices, standards and guidelines for various medical practice areas. The knowledgebase 21 includes rules that represent best practices, standards and guidelines, including the specific treatments, diagnoses and essential documentation available for an ailment that has been judged optimal after analyzing the items of patient information. The knowledgebase 21 includes various protocols and pathways of care including, clinical, risk management, administrative, financial, and legal management pathways. Moreover, because treatment pathways vary among practitioners and institutions, the knowledgebase 21 can be customized to a medical facility's clinical standards, guidelines and support services. It is contemplated that the knowledgebase 21 can be updated to reflect the most current best practices, standards and clinical guidelines.

The central monitor 17 is located at a central location, such as a nurses' station in a hospital. The central monitor 17 includes a processor, memory, and one or more input and/or output (I/O) devices (or peripherals) that are communicatively coupled via a local interface.

The workstations 15 are located in patient treatment areas, such as patient rooms, emergency rooms, operating rooms, or other areas that patients receive treatment. Each workstation 15 includes a processor, memory, and one or more input and/or output (I/O) devices (or peripherals) that are communicatively coupled via a local interface. As will be described herein, the medical record computer program with support and compliance capabilities executed via the workstation 15.

Figure 9A:
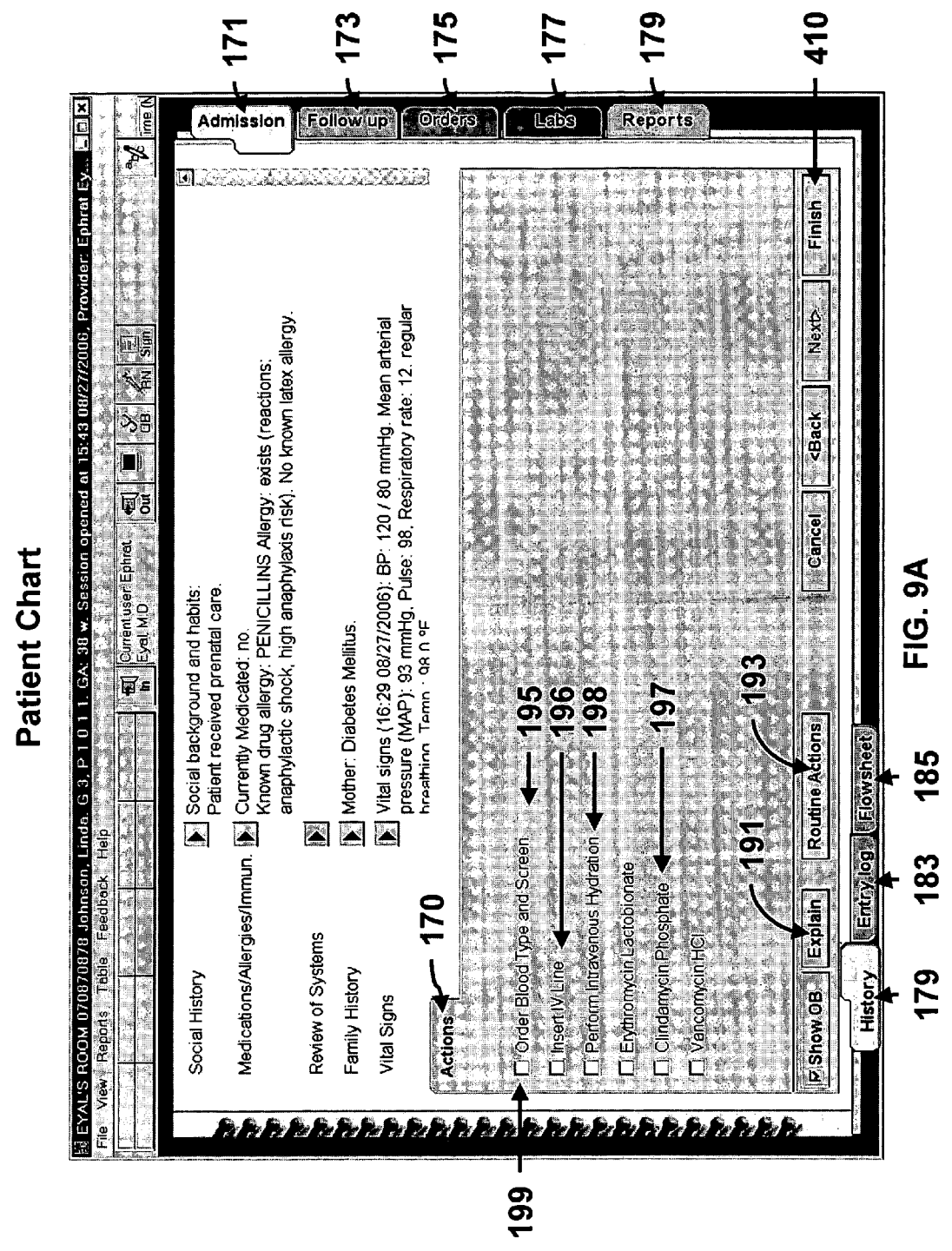

FIG. 9A illustrates the interface on the workstation 15 for the medical record computer program with support and compliance capabilities. The interface includes an Admission tab 171, a Follow Up tab 173, an Orders tab 175, a Labs tab 177, and a Reports tab 179. The interface also includes a History tab 181, an Entry Log tab 183, and a Flowsheet Tab 185.

FIG. 3 illustrates a screenshot of an electronic medical record 23 in the patient care system 10 under the Admissions tab 171. Typically, the electronic patient record 23 is displayed on the display of the workstation 15; however, it can also be displayed on the central monitor 17. The electronic medical record provides items of patient data 24 pertinent to a specific clinical situation and permits medical staff to document critical information and accurately manage a patient's care. For example, in obstetrics the items of patient information can include patient demographic 25, patient admission information, dating/number of fetuses 27, obstetric history 29, chief complaint, antepartum course 31, and prenatal labs 33, and prenatal clinic evaluation. Patient information on the electronic medical chart may be edited by selecting an icon 24 associated with a respective item of patient information.

Figure 4:
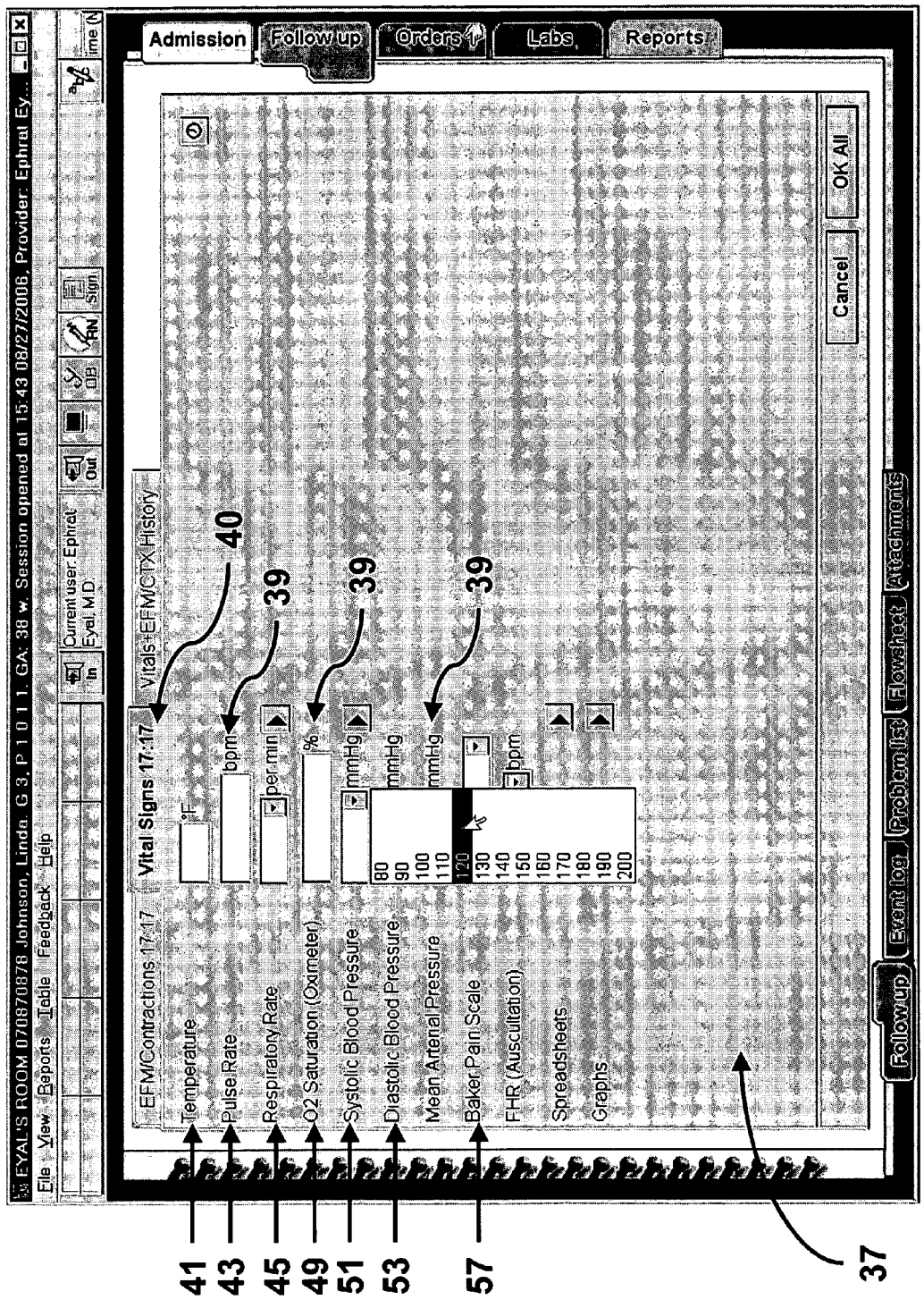
Figure 5:
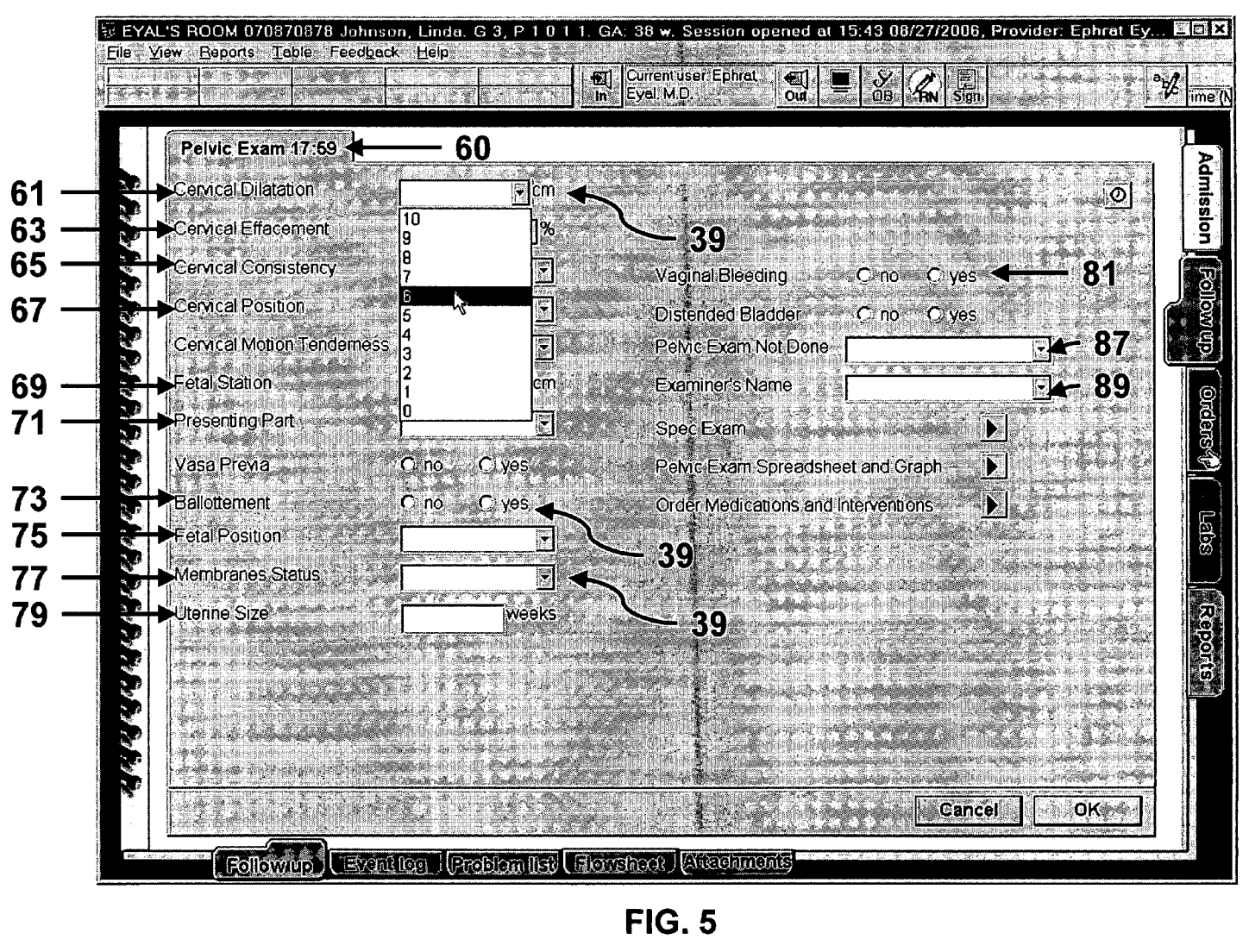
Figure 6:
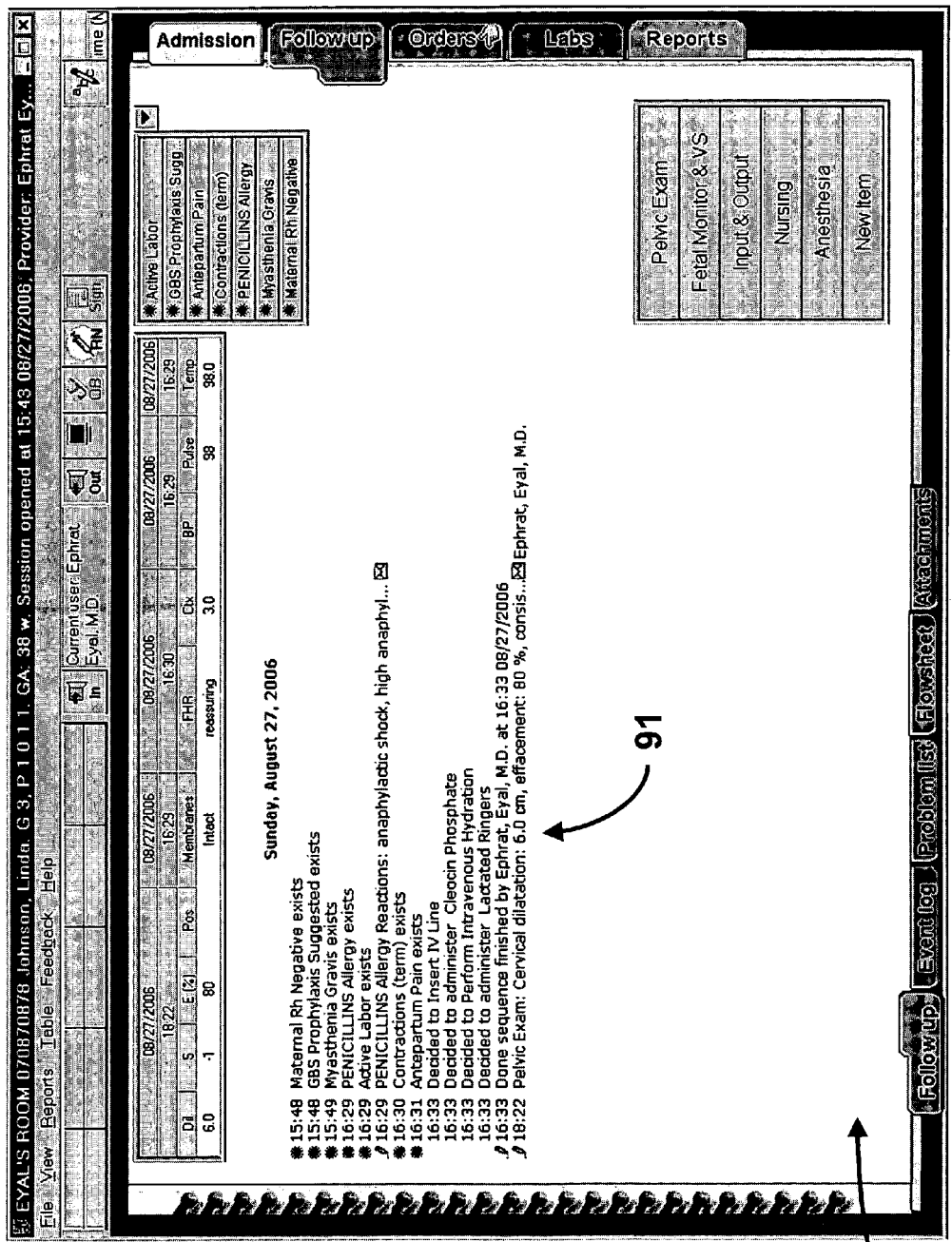

As illustrated in FIG. 4 and FIG. 5, items of patient data may be entered into the patient care system 10 using an entry form 37. The patient data may include patient information, an action, a decision, or a diagnosis. The patient information can also include whether a diagnosis has been diagnosed, a decision has been reached, and an action has been completed. The entry form 37 includes a tab that corresponds to a type of patient information such as vital signs 40, as seen in FIG. 4, or pelvic exam 60, as seen in FIG. 5. The entry form includes patient information fields 39 for entering items of patient information. For example, the items of patient information for vital signs can include temperature 41, pulse rate 43, respiratory rate 45, 02 saturation 49, systolic blood pressure 51, diastolic blood pressure 53, and pain scale 57. As seen in FIG. 5, the items of patient information for a pelvic exam can include cervical dilation 61, cervical effacement 63, cervical consistency 65, cervical position 67, fetal station 69, presenting part 71, ballottement 73, fetal position 75, membranes status 77, uterine size 79, vaginal bleeding 81, pelvic exam not done 87, and examiner's name 89. As shown in FIG. 6, once the appropriate items of patient data are entered, the system presents the information in a readable format 91 in the patient chart 23.

The medical record computer program with support and compliance capabilities includes a Compliance Adhering Mechanism (CAM). The program 112 evaluates the entered items of patient data, at any point of the patient care with a set of more than 6,500 best practice rules, guidelines and protocols and generates a list of items that are required by the system 10 for providing the best documentation, decisions and diagnoses, pertinent to the specific case, and based on the hospitals best practice guidelines. The best practice rules, guidelines and protocols are programmed into the system during its implementation phase, are customizable to represent the hospital's care guidelines. If the computer program 112 determines that items of patient data are missing, the program 112 generates a notification 93 and displays the notification 93 on the display of the workstation 15, as shown in FIG. 7H.

The notification 93 identifies the missing items of patient data. For example, the missing items of patient data can be Pelvic Adequacy (Clinical) 131, Current Pregnancy Serology 133, EFM/Contractions 135, and more. It is contemplated that each missing item of patient data is associated with a hyperlink. When a hyperlink for a missing item of data is selected, a field is generated that allows the missing item of data to be completed. Hyperlinks limit the need for searching this particular item of data entry within the patient chart.

Figure 7A:
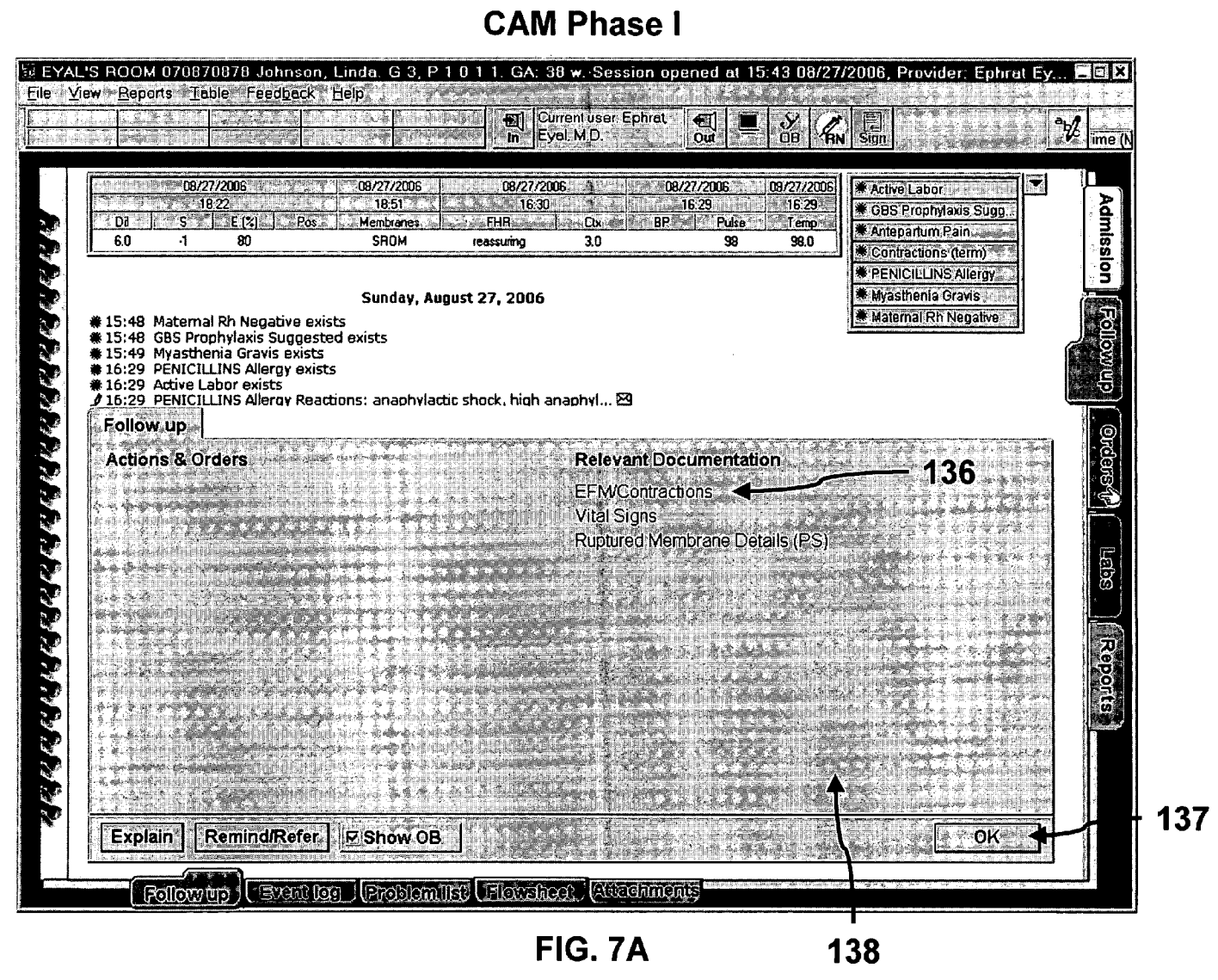

If the missing item of information, action, decision or diagnosis is not completed after a predetermined time, and its criticality becomes higher, based on the hospital's best practice guidelines, the program 112 activates its CAM Phase I and will start prompting for this item at certain time intervals, based on its criticality, alerting the clinical staff that this missing item of information, action, decision or diagnosis is still missing, as shown in FIG. 7A. In one example, when the patient ruptures its membranes (SROM=Spontaneous Rupture Of Membranes), a hospital best practice guideline may be to require the evaluation and documentation of the fetal heart rate and fetal status immediately after that event. The need to do this originates from the risk that the umbilical cord may be compressed between the fetus and the mother's bony pelvis, due to the lack of amniotic fluid after the membranes broke. A compression on the umbilical cord may cause a blockage of blood and oxygen supply to the fetus that may result in asphyxia and injury to the fetus. In such an event, the fetus enters into a state of fetal distress, which may be detected in the fetal heart rate monitoring. The patient record prompts for the evaluation and documentation of EFM/Contraction 136. However, if the staff do not enter this information and click the OK button 137, dialog 138 disappears but the patient record will prompt again for item 136 with dialog menu 138 after 5 minutes, to alert and remind the clinical staff of the importance and criticality of this information.

While workstation 15 prompts for the critically missing item at the certain time interval, after certain number of prompts, based on the clinical significance of the missing item, the system will activate its CAM Phase II, in which the central terminal 17 will present a red alert notification around the patient name 139 and on the patient's room button 140, to indicate that there is a critically missing items for that particular patient. The central terminal 17 can be located at the central nurses stations, at the physicians' room and/or at any centrally/controlling location. The central terminal 17 presents the upgraded notification to the clinical/administrative staff as show in FIG. 7B. For example, if EFM/Contractions documentation has not been documented after 10 minutes from the SROM (after 2 prompts 136 that appeared at 5 minutes interval), the patient's name 139 at the central terminal starts blinking in red as well as the patient's room 140. Clicking on either the patient name 139 or the patient's room 140 will open a notification dialog 141 which will show the critically missing item 142. Both the repeating prompts 136 and the red alert notifications 139 and 140 will continue prompting until all the missing item of information, action, decision or diagnosis is completed.

Figure 7C:
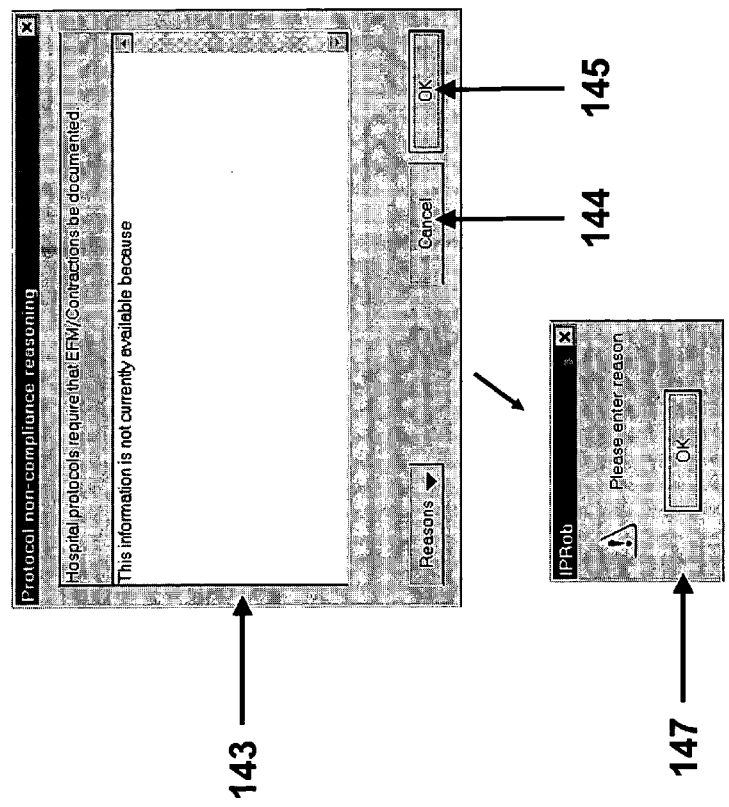
Figure 7D:
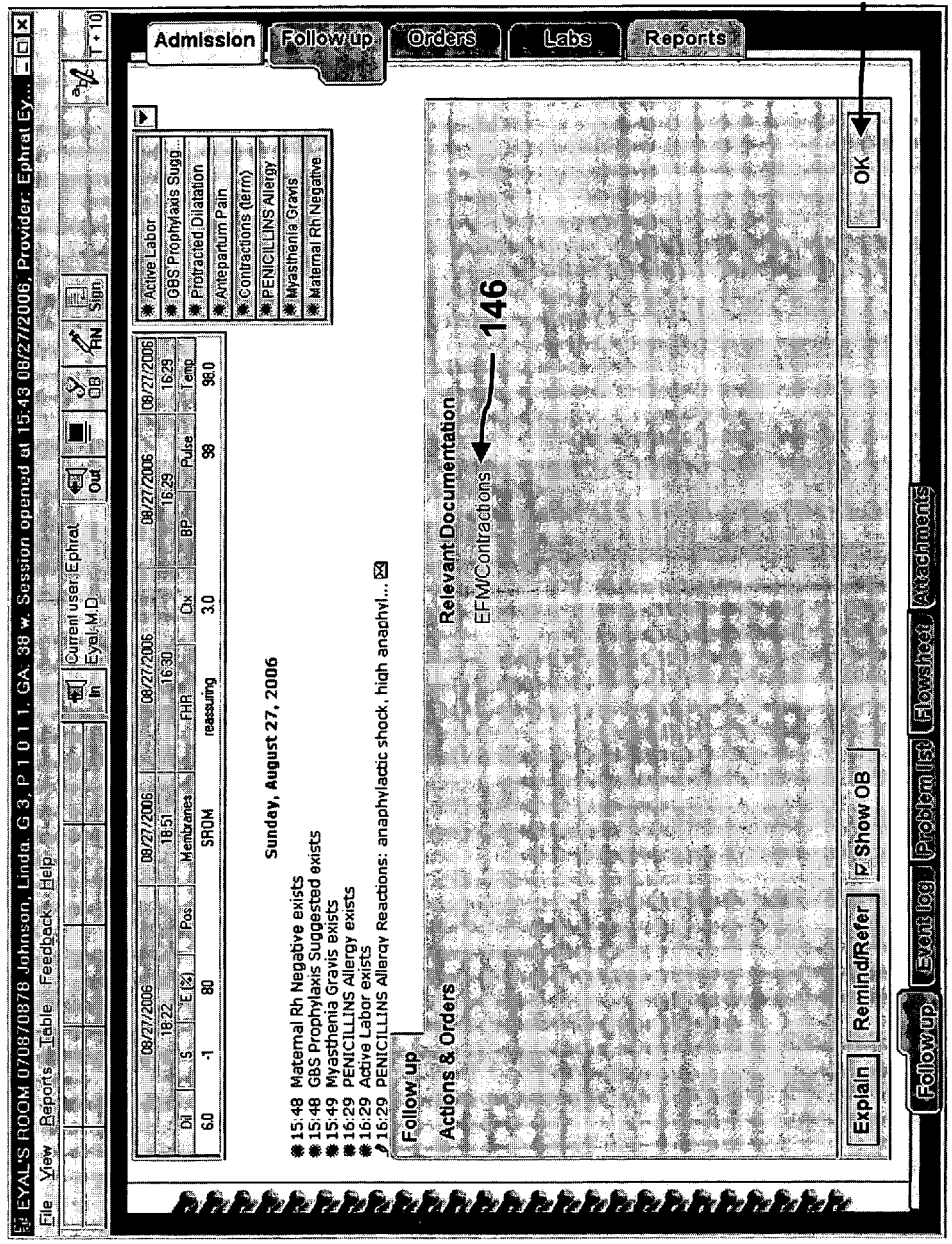
Figure 7E:
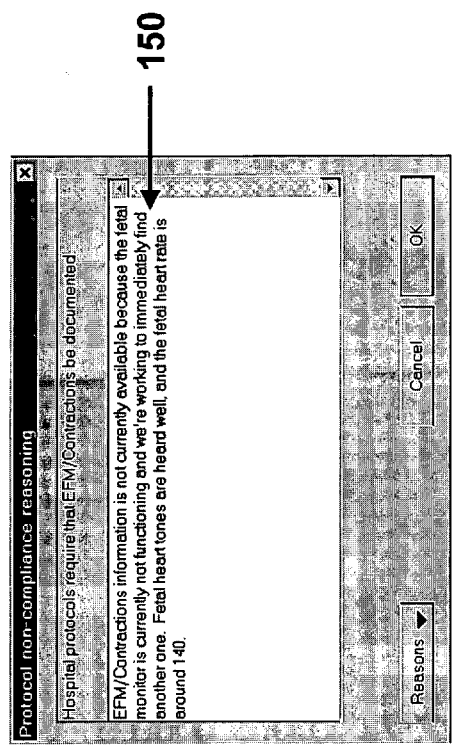
Figure 7F:
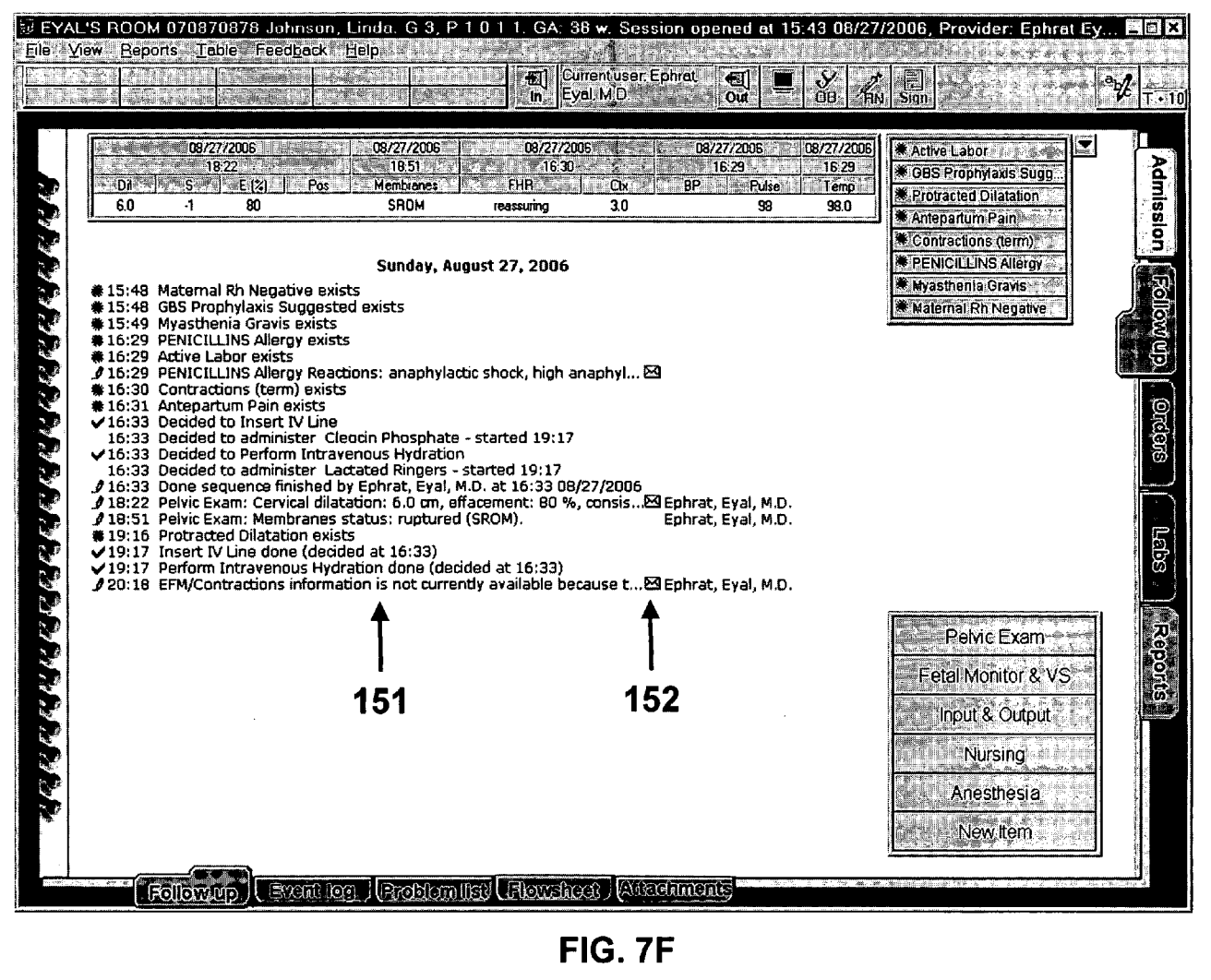
Figure 7G:
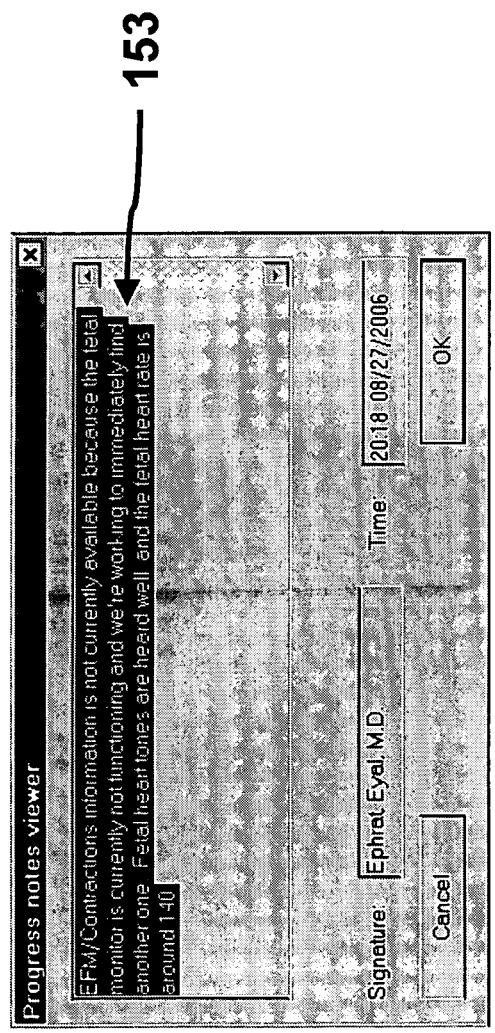
Figure 7H:
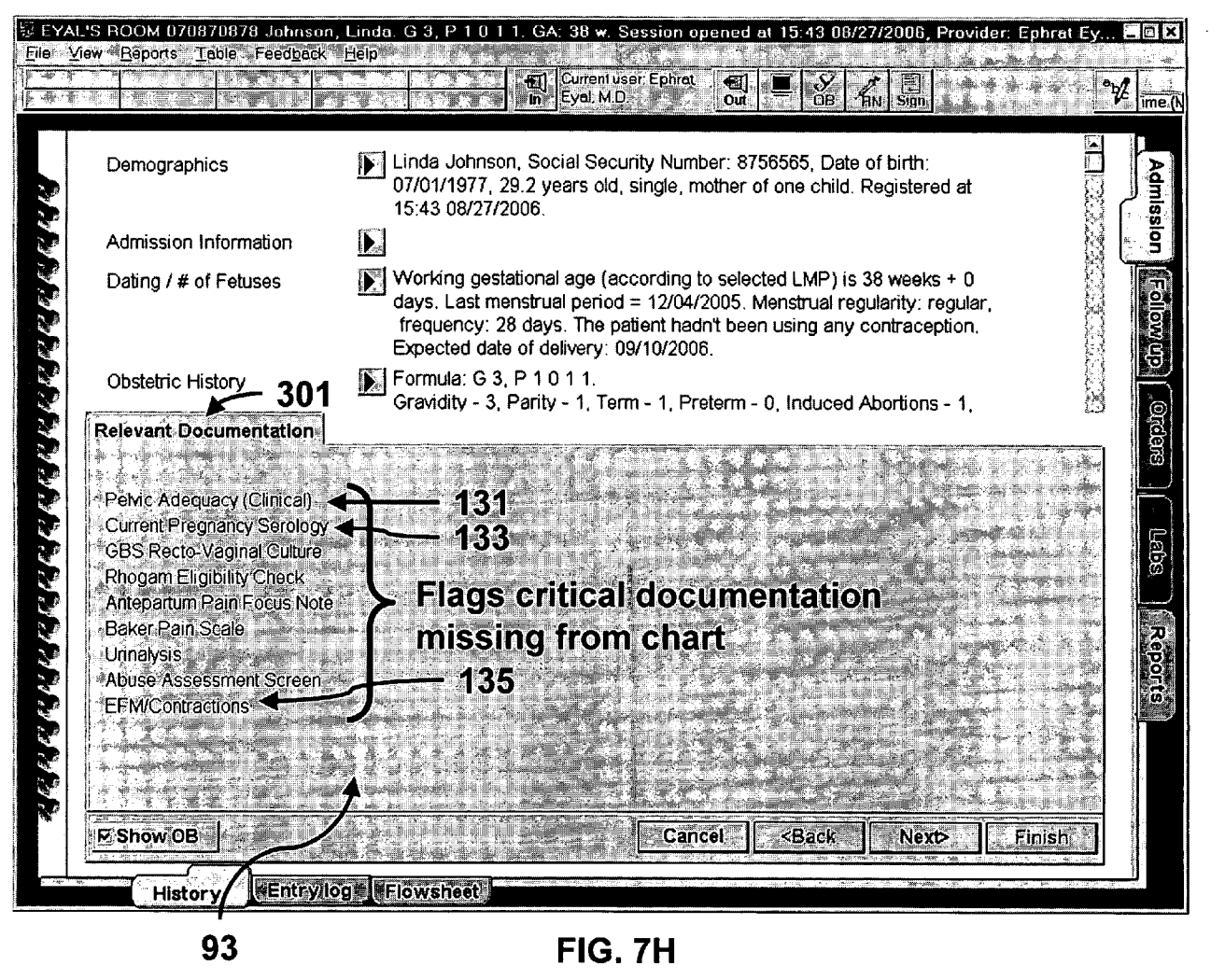

If the missing item of information, action, decision or diagnosis is not completed after a predetermined number of notifications have been generated and displayed, the system will activate its CAM Phase III, in which a final notification having a mandatory explanation dialog 143 will be generated and displayed on the patient record, as presented in FIG. 7C. The final notification remains on the screen until a reason explaining why the missing item of information, action, decision or diagnosis has not been completed, is entered in the explanation field. If the user selects the Cancel button 144, the missing critical item 146 required for documentation is immediately presented to the user, as illustrated in FIG. 7D. However, if the user selects the OK button 145 or the OK button 148 without entering and reasoning why this item has not been documented, the system will present the alert 147, notifying the user that the reasoning of the missing item has not been entered and needs to be entered. For example, if the SROM patient did not have a documentation of EFM/Contractions after 15 minutes, the reasoning dialog 143 will appear, mandating the staff member to either enter the missing item or enter the explanation of not doing so. Through this compliance mechanism, after a certain period of time the user, when logging into the system, will have to enter the missing item or enter and explanation for the reason not to do so. An example of an explanation text 150 the staff can enter is illustrated in FIG. 7E, and presented in the patient chart 151, as shown in FIG. 7F. Clicking on envelope 152 opens an expanded window 153 with the complete explanation entered by the staff, as shown in Fig. FG.

In addition, the notification can include a "Reasons" button. Selecting the "Reasons" button displays a list of predetermined reasons that a user may select to be entered in the explanation field. Once the explanation is entered, the user selects the "OK" button.

Figure 8A:
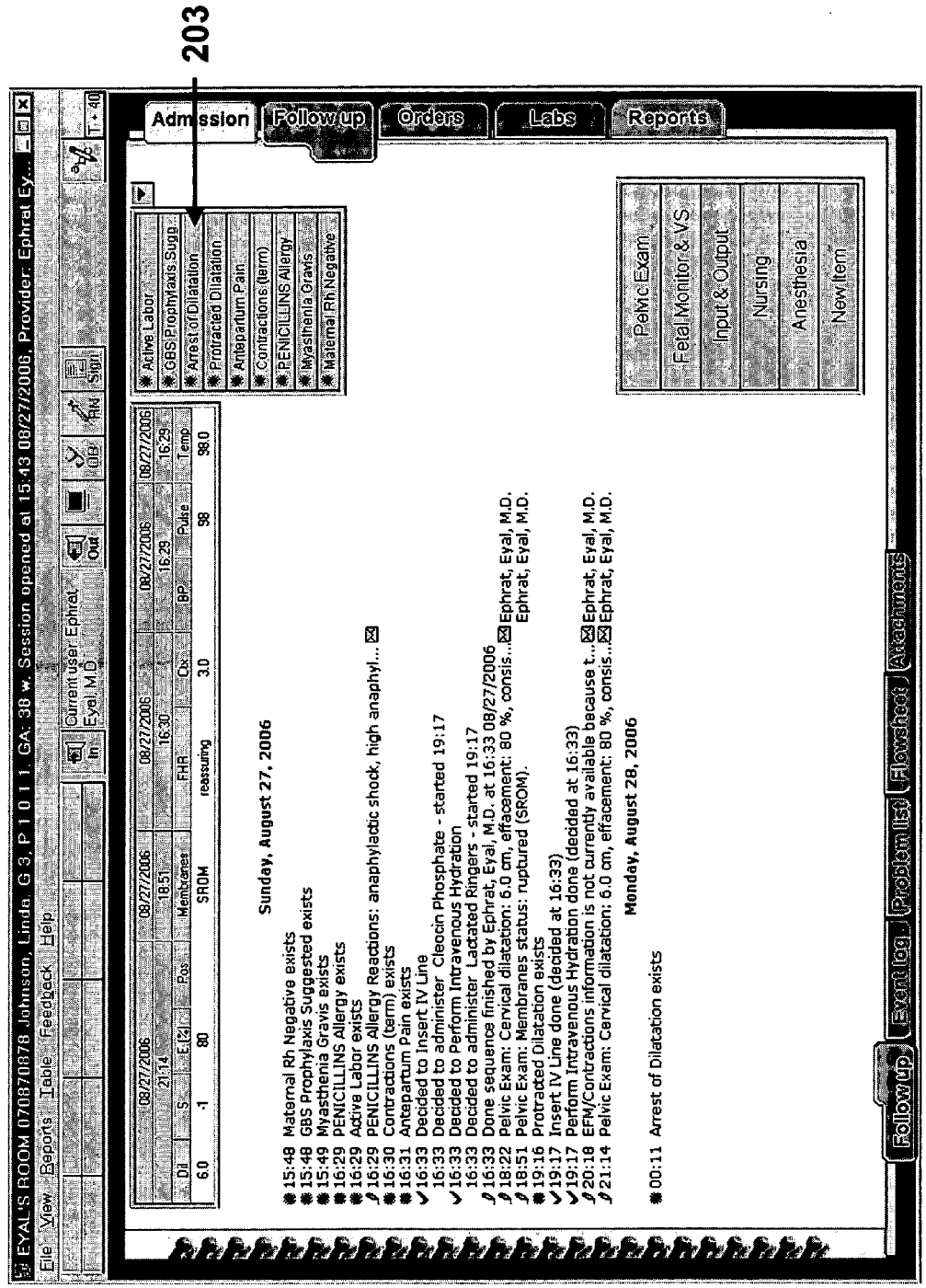
Figure 8B:
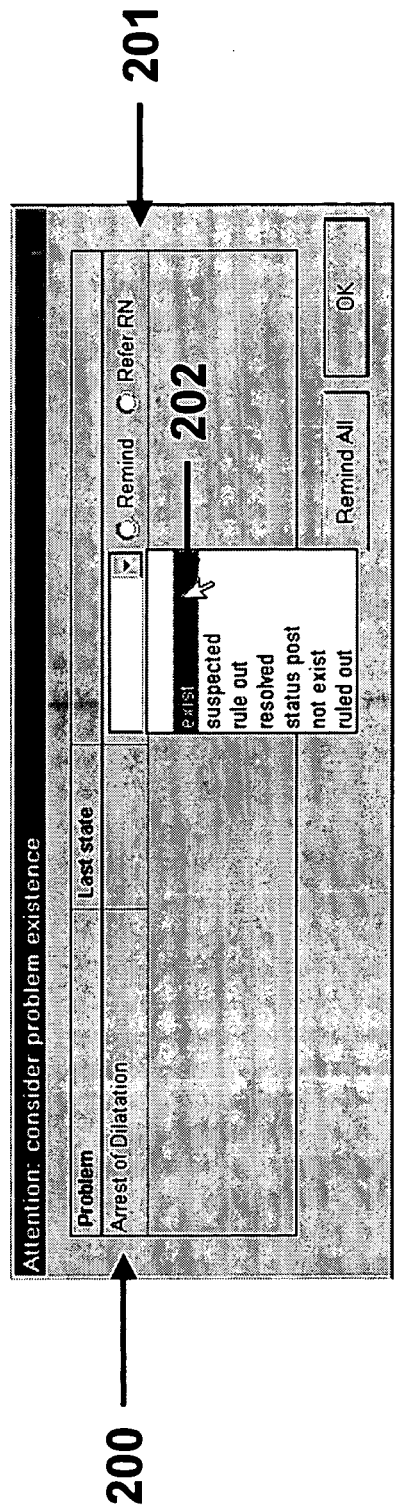

The program 112 continuously analyzes the received information, actions, decisions and diagnosis items and determines further suggested information, decisions, actions or problems that the staff may need to enter, based on the specific clinical situation of the patient and based on the hospital's best practices. The program 112 may present actions the staff should consider performing, as presented in FIGS. 9A and 9B, or suggested problems the staff should consider, as presented in FIG. 8B. The suggested problem 200 is displayed in a dialog 201 on the display of the workstation 15, as shown in FIG. 8B. If the suggested problem exists the staff should select the "Exists" state from the pull-down 202. This problem is then presented in the patient chart's problem list 203 as a problem that exists.

Based on the diagnosed problems and received items of patient information, the computer program 112 determines appropriate actions by comparing the diagnosed problems with the system's best practice rules and guidelines. The appropriate actions are displayed in an Actions tab 170 on the display of the workstation 15, as shown in FIG. 9A. The Actions tab includes an "Explain" button 191 and a "Routine Actions" button 193.

The list of appropriate actions can include perform Order Blood Type And Screen 195, insert IV line 196, cindamycin phosphate 197, Perform Intravenous Hydration 198, etc. A field 199, such as a check box, is associated with each respective action. A user indicates that an action should be performed by selecting the respective field 199 associated with the action.

Figure 9B:
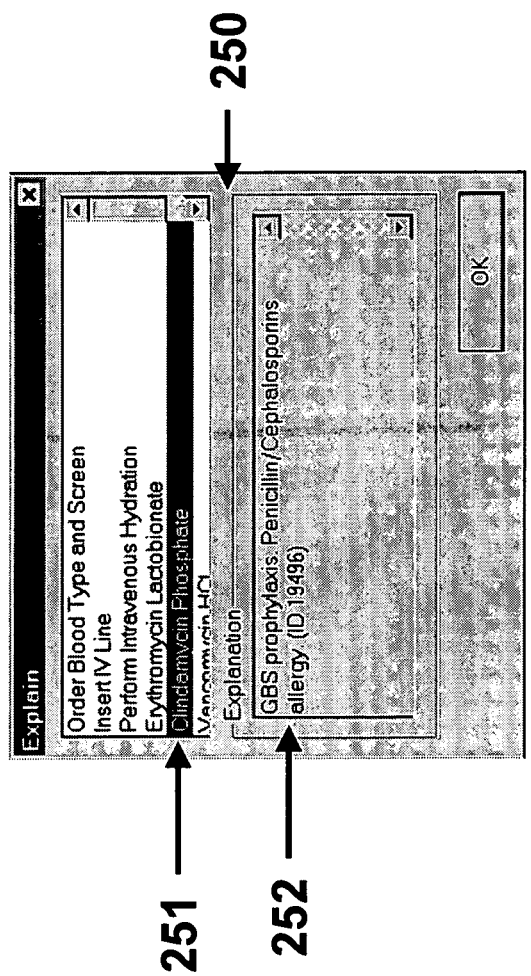

As noted, the Actions tab 170 includes an "Explain" button 191. Selecting the "Explain" button 191 generates and displays a dialog box 250 listing the suggested actions that appear on the screen, with the explanation for the reason each of them appear in the suggested list, based on the hospital's best practice rules, guidelines and protocols. An example of the dialog box 250 is illustrated in FIG. 9B. Once an action that needs to be performed is selected 251, the dialog box presents the reasoning text in the window 252 below.

Admission Tab

The Admission Tab, as shown in FIG. 3 presents the patient information 25, 27, 29, 31, 33 and more, as collected and entered by the clinical staff, associated with the patient's historic information, clinical background and historic diseases as well as the status of its current illness and reason for visiting the hospital. The Admission Tab also holds information about the initial evaluations and examinations performed on the patient before a decision is made on the patient's further treatment and management of the case.

Once the clinical staff has finished with the data entry and initial evaluation of the patient and is ready to make the decisions regarding the patient's treatment and management, the staff clicks the Done button 300, as shown in FIG. 3, and initiates the Done Sequence. The Done Sequence is a cascade of system presented screens that lead the staff through the case evaluation process, assuring that important information items, actions, decisions and diagnoses are appropriately considered and entered into the system.

Figure 10A:
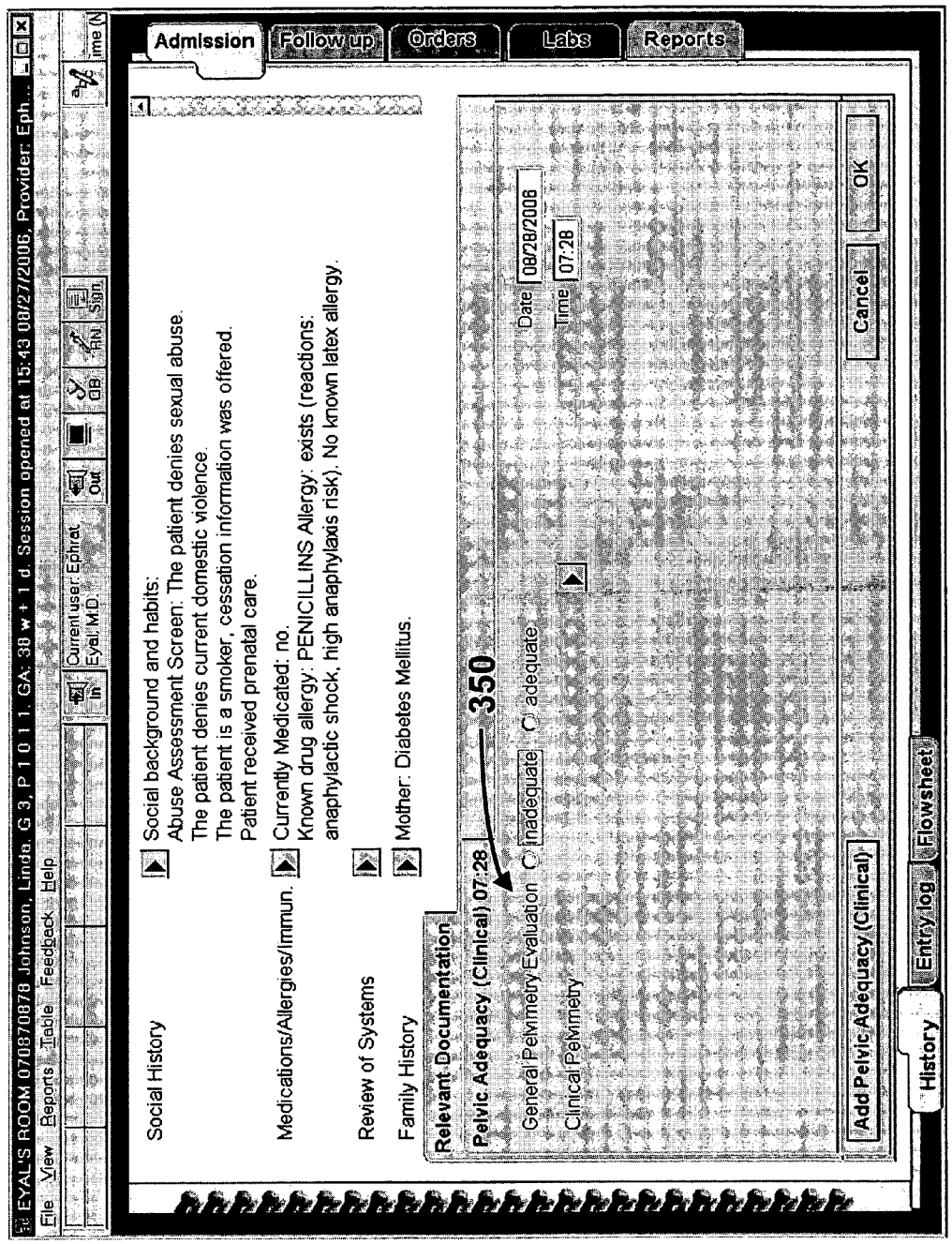
Figure 10B:
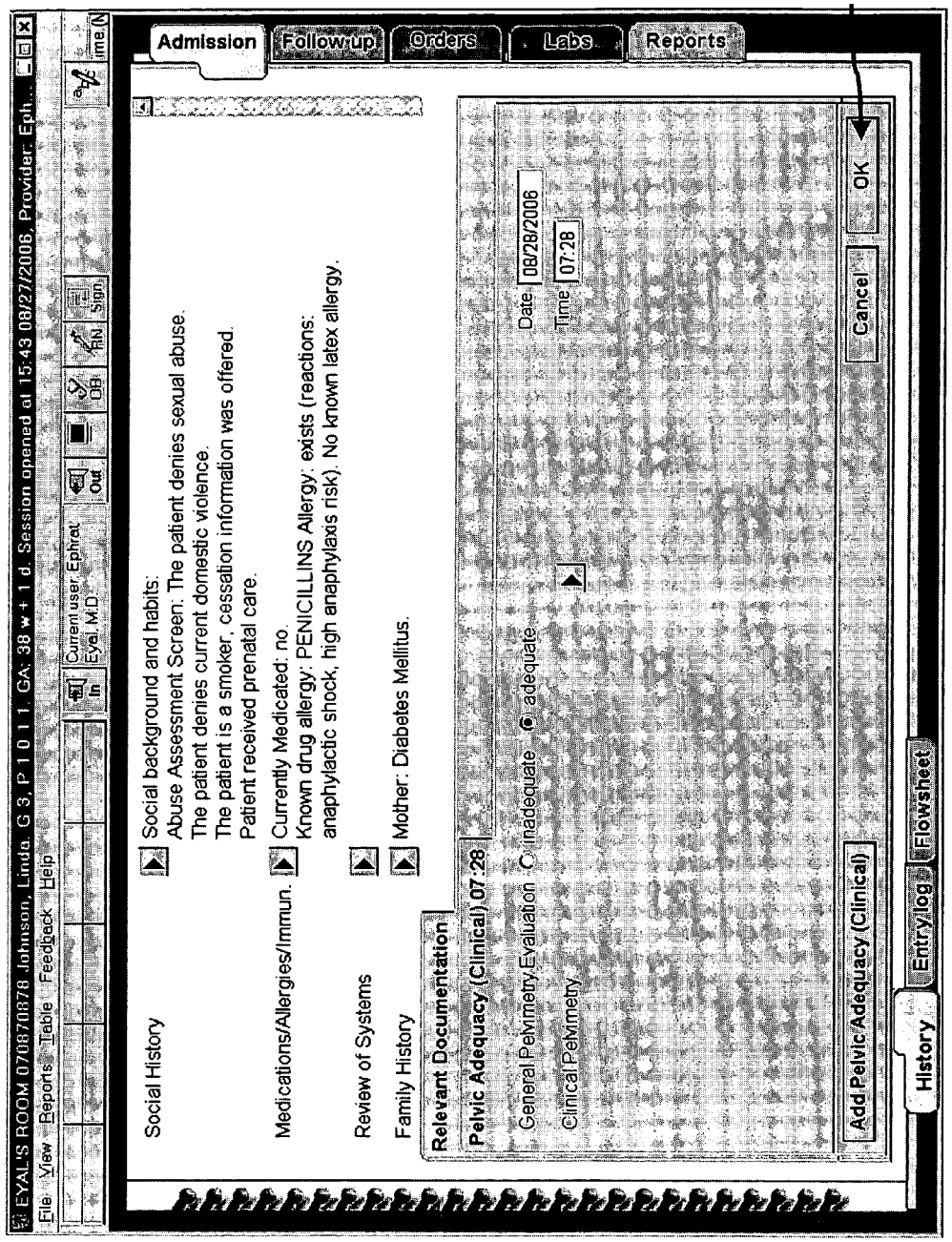
Figure 10C:
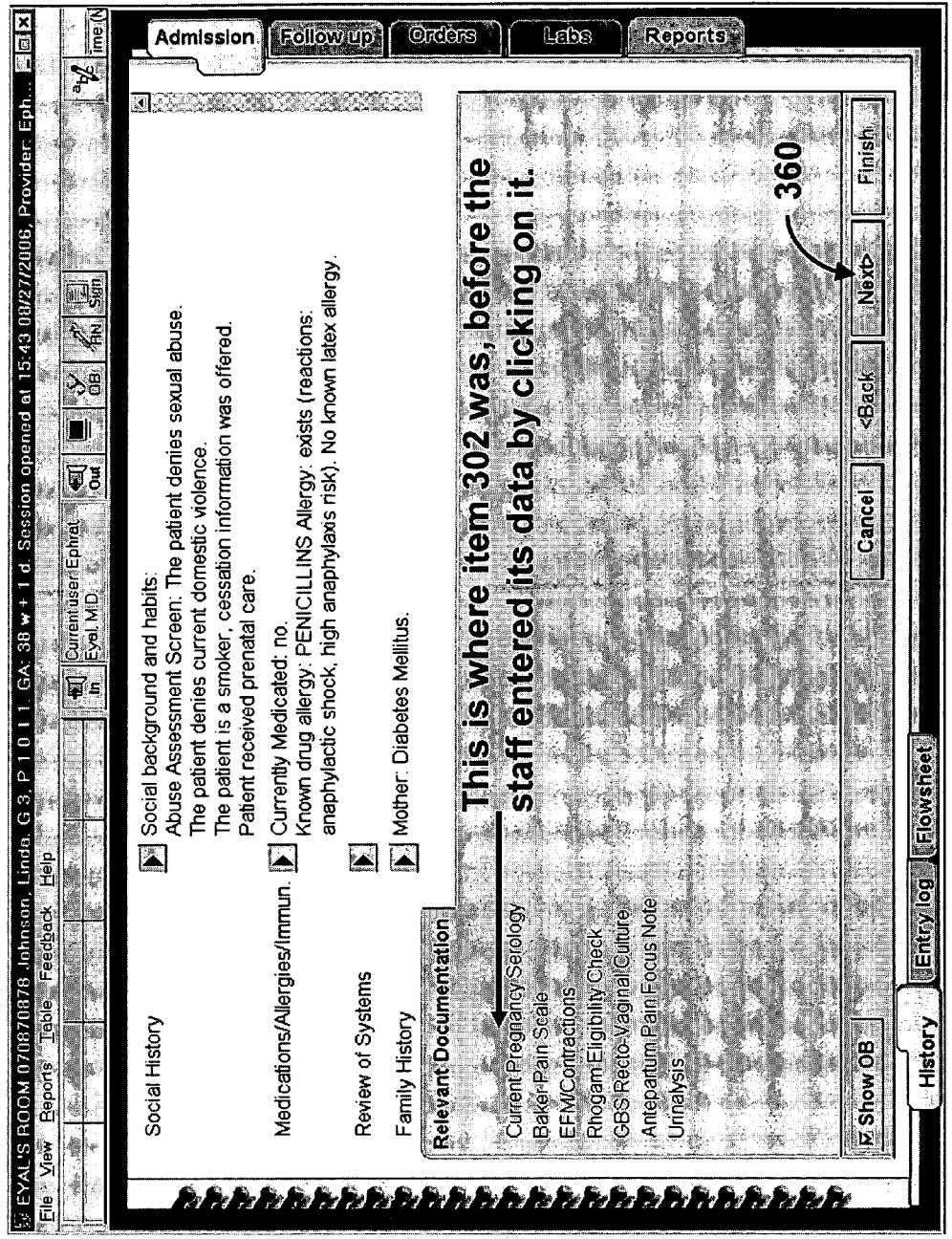
Figure 10D:
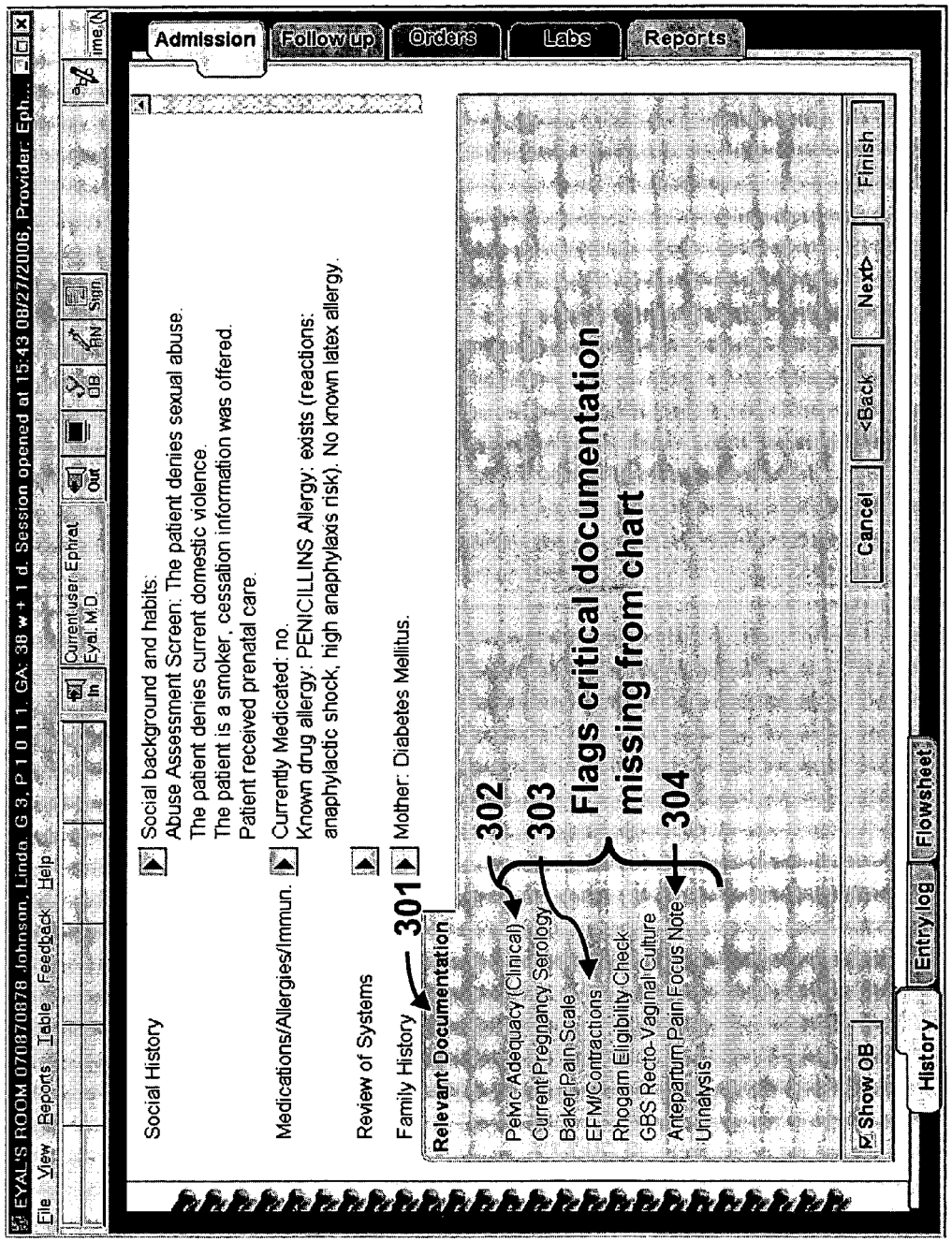

The first screen that appears during the Done Sequence is the Relevant Documentation screen 301, as shown in FIG. 10D. This screen presents highly important documentation items 302, 303, 304 and more, that are currently missing in the chart and needed for appropriately managing the specific patient situation. These items are generated by the system through the evaluation of the data already existing in the chart and the rules, guidelines and protocols existing in the system representing the best practices of the hospital. Clicking on any of the presented missing items brings up the entry field 350 for data entry to such item, as shown in FIG. 10A. Entering the data to field 350, as shown in FIG. 10B, and clicking the OK button 351 will satisfy the need for this information and will erase this missing item from the missing items list in the Relevant Documentation screen 301, as shown in FIG. 10C. Through this Active Menu Generation mechanism, the staff will be notified on missing items and will enter them without the need to search in the patient chart for the location of this item.

Figure 11:
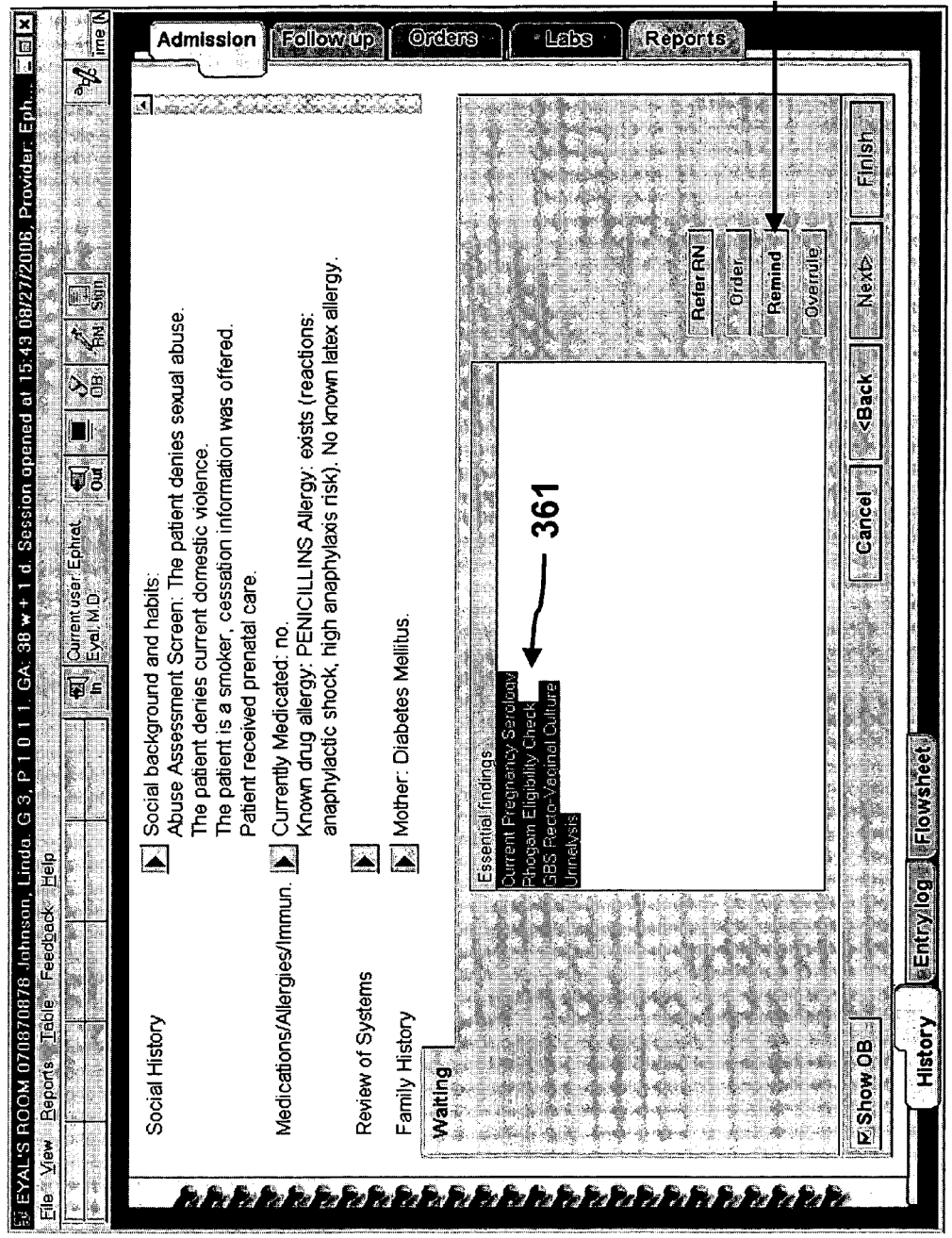

Once the staff finished entering the important missing information, based on the specific clinical situation, he/she clicks the Next button 360. If items still exist in the missing list of the Relevant Documentation 301, the system will present a dialog box 361 alerting of these missing items, as shown in FIG. 11. The staff can either click any of the items presented in this window or click the Remind button 362 to move those items to the Wait list for later attendance.

Figure 12:
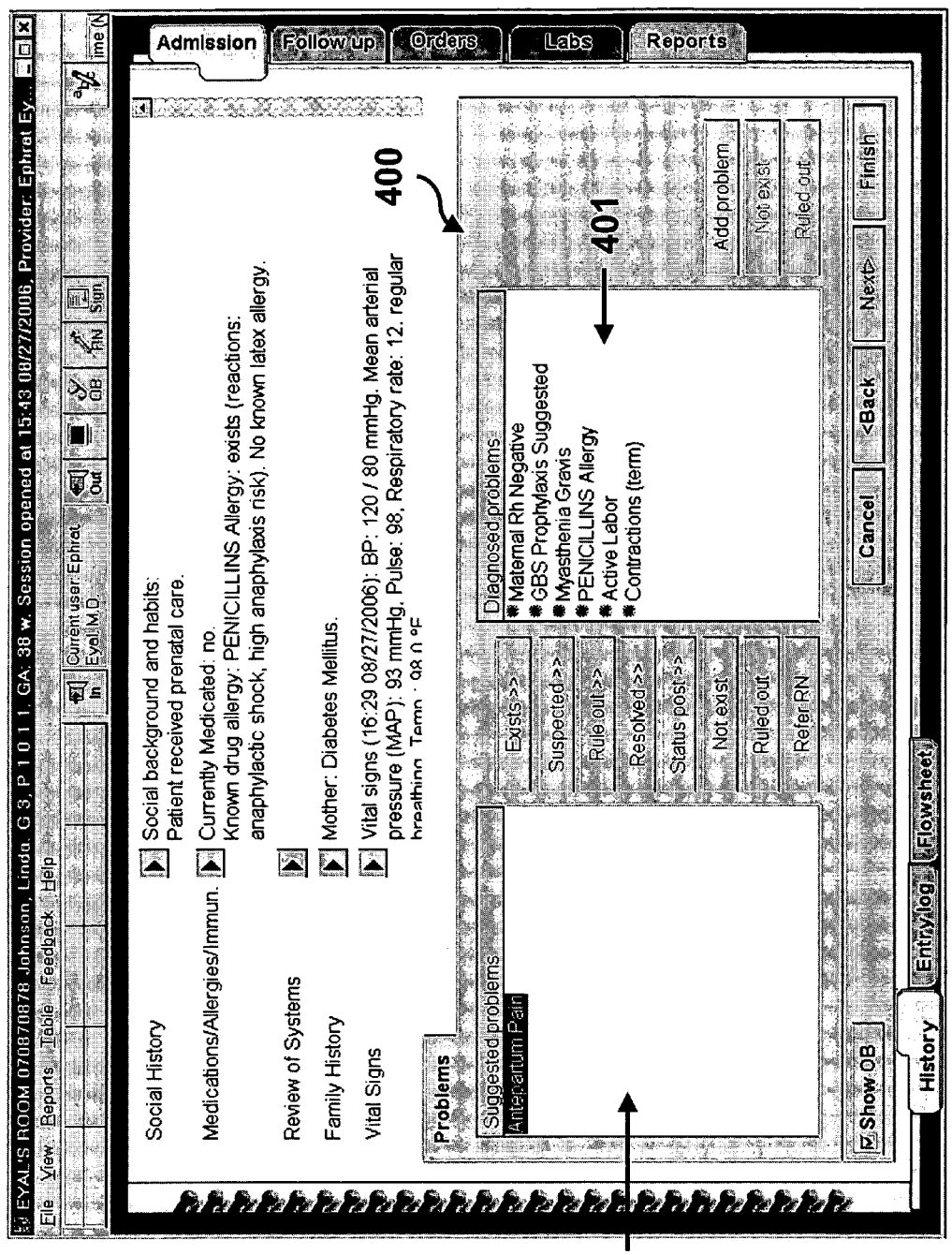

The next screen of the Done Sequence is the Problems screen 400, as shown in FIG. 12. This screen presents the relevant diagnoses and problems the patient has relevant to the current clinical situation and based on the best practices guidelines of the organization. Window 401 presents problems the system already declares as exist, based on the hospital's best practice guidelines and the window 402 presents problems the staff may need to consider based on the staff's clinical judgment.

The next screen of the Done Sequence is the relevant Action screen 170, as shown in FIG. 9. This screen presents the Actions the staff should consider taking, based on the hospital's best practice rules, guidelines and protocols. Clicking the Finish button 410, end the Done Sequence and automatically opens the Follow-Up tab.

Follow Up Tab

Figure 13:
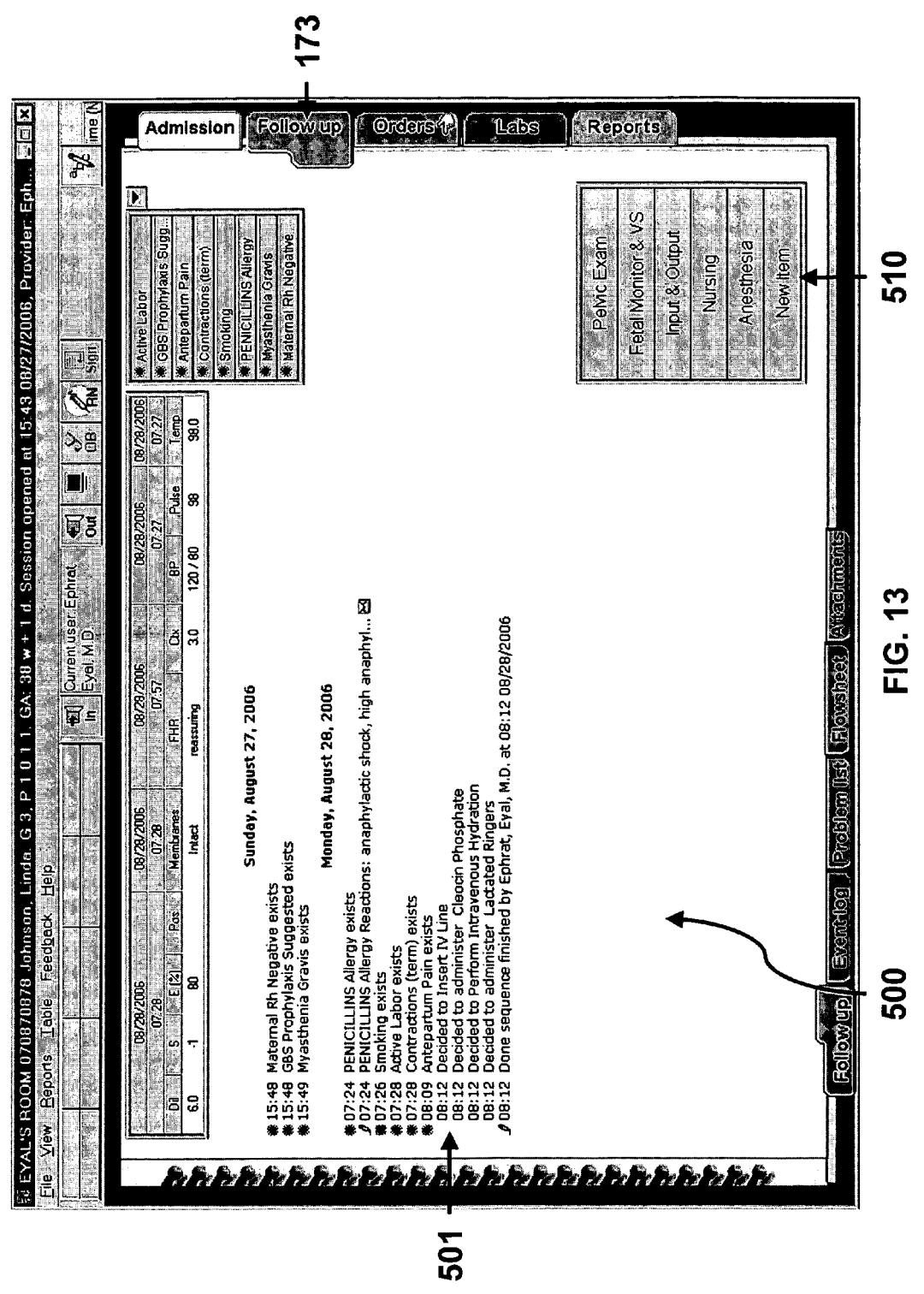

Once the Finish button 410 is clicked, a follow up interface 500 showing schedule information 501 under the Follow Up tab 173 is displayed on the display at the workstation 15, as illustrated in FIG. 13. It is noted that the Follow Up tab 173 may also be viewed by selecting the tab on the display. The schedule information 501 includes the existing and non-existing diagnosed problems 401 under the problems tab 400 and the date and time the diagnosed problems 401 were determined and inputted into the system 10. The schedule information also includes the actions that were decided to be performed as well as the information items that were documented, including the date and time these actions and information items were determined to be performed or documented. New information, action, decision or problem, related to a particular category 510 can be added to the schedule information by selecting the appropriate category that needs to be added. An example of a category 510 can be pelvic exam, fetal monitor and VS, nursing, anesthesia, or a new item.

Figure 14A:
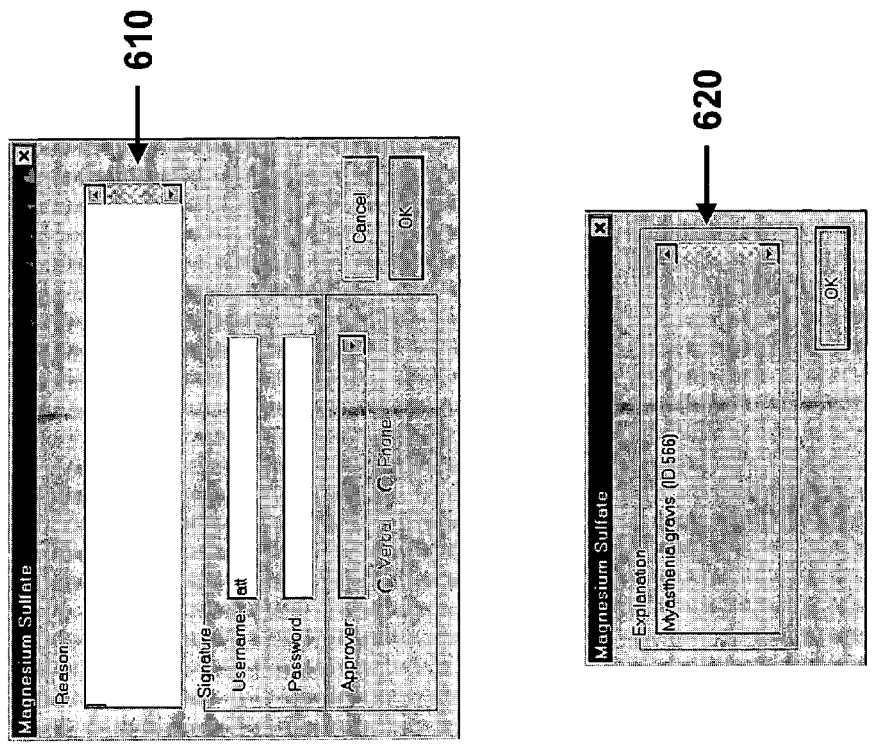
Figure 14B:
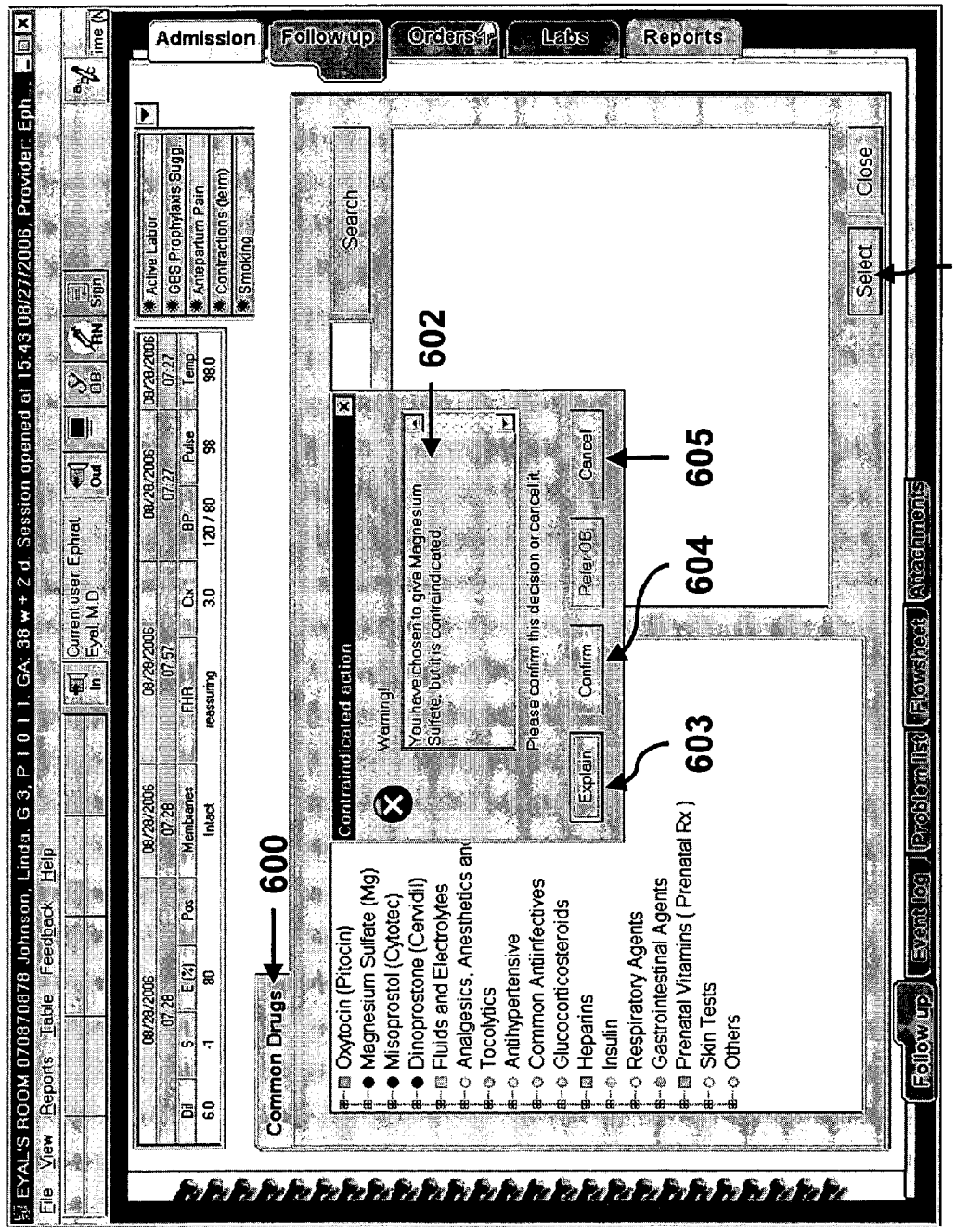

One of the actions that may be performed is drug administration. As illustrated in FIG. 14B, a user can indicate a particular drug that should be administered using a "Common Drugs" tab 600. The user highlights a drug from the list and selects the "select" button 601 to indicate that the selected drug should be scheduled to be administered. The program 112 determines if the selected drug is suitable for administration to a particular patient by analyzing the items of patient data for the particular patient's clinical situation and the rules of best practice stored in the database 21. If the drug is unsuitable/contraindicated for administration to the patient, based on the best practice guidelines of the hospital, a notification 602 is generated and displayed. Based on the reason for selecting this particular drug, the user may select a "confirm" button 604, a "cancel" button 605, or an "explain" button 603. Selecting the "confirm button" 604 confirms that the drug should be administered and scheduled for administration. In such a case, as shown in FIG. 14A, a Reasoning Dialog 610 opens, mandating the staff to provide their reasoning for selecting a contraindicated drug. This is mandatory as the staff may make an error in selecting this drug, according to the best practice guidelines of the hospital, and the reasoning for proceeding with this drug is, therefore, mandatory to be documented in order to substantiate the staff's reason to do so. The staff may also select the "cancel" button 605 which cancels the scheduled administration of the drug. Selecting the "explain" button 603 opens window 620, as illustrated in FIG. 14A allowing the user to provide the reasons, based on the hospital's best practice guidelines, of why the drug is contraindicated for administration.

Orders Tab

Figure 15:
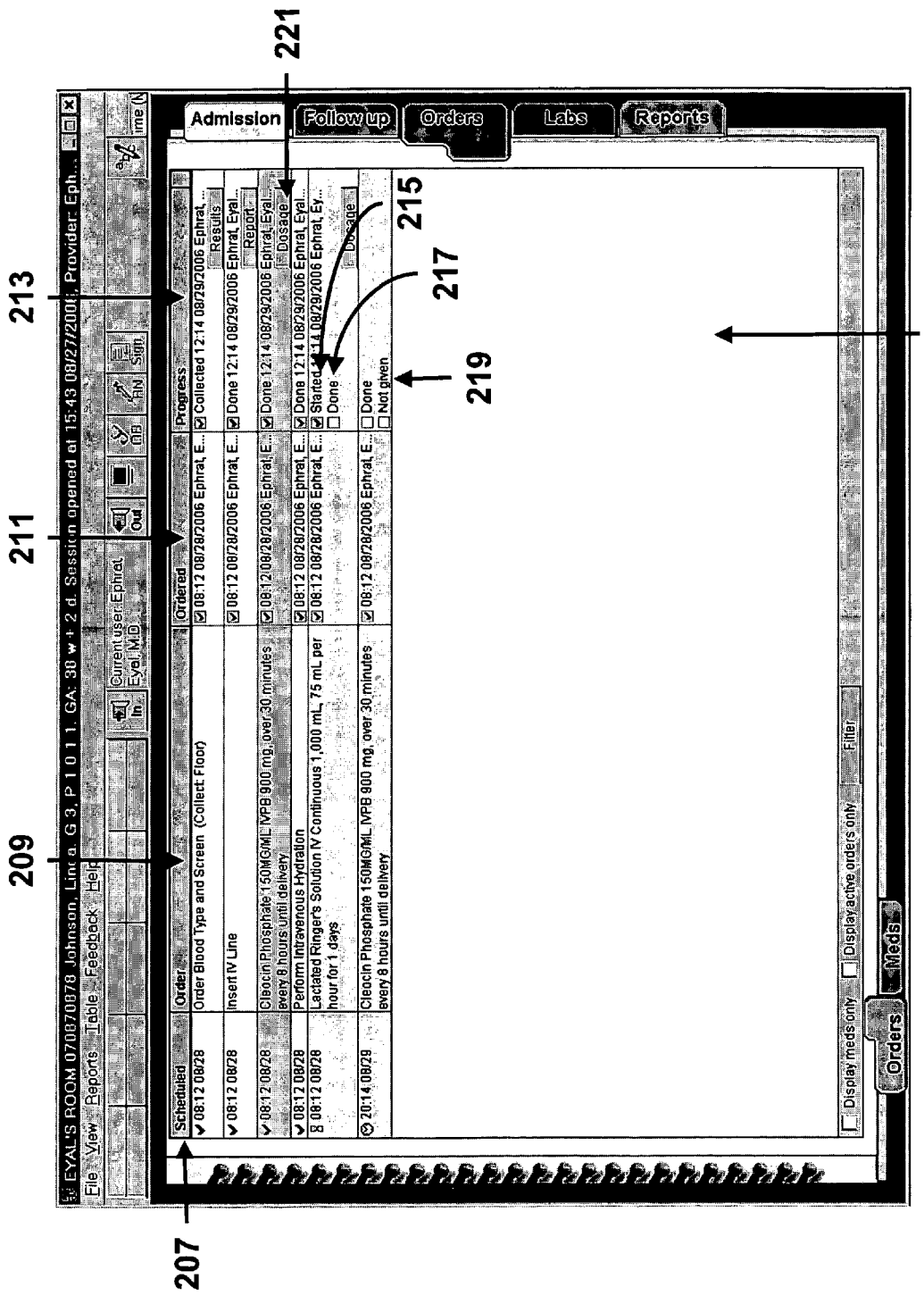

FIG. 15 illustrates a screenshot of the order interface 205 under the Order tab 175 in the patient care system 10. The order interface 205 includes a table having a schedule information column 207, an order information column 209, an ordered information column 211, and a progress information column 213 for displaying the status of the order. Each cell in the schedule information column 207 indicates the date and time an action is scheduled to be performed. Each cell in the order information column 209 identifies the action that needs to be performed and each cell in the ordered information column 211 indicates the date and time the respective action was ordered.

The cells in the progress information column include indicators for indicating whether a respective action has been started 215, whether an action is done 217, or whether an action is not done 219. In addition, the cell can contain a selectable "Dosage" button 221 for allowing a user to enter the dosage of medication that was given pursuant to the action.

Figure 16:
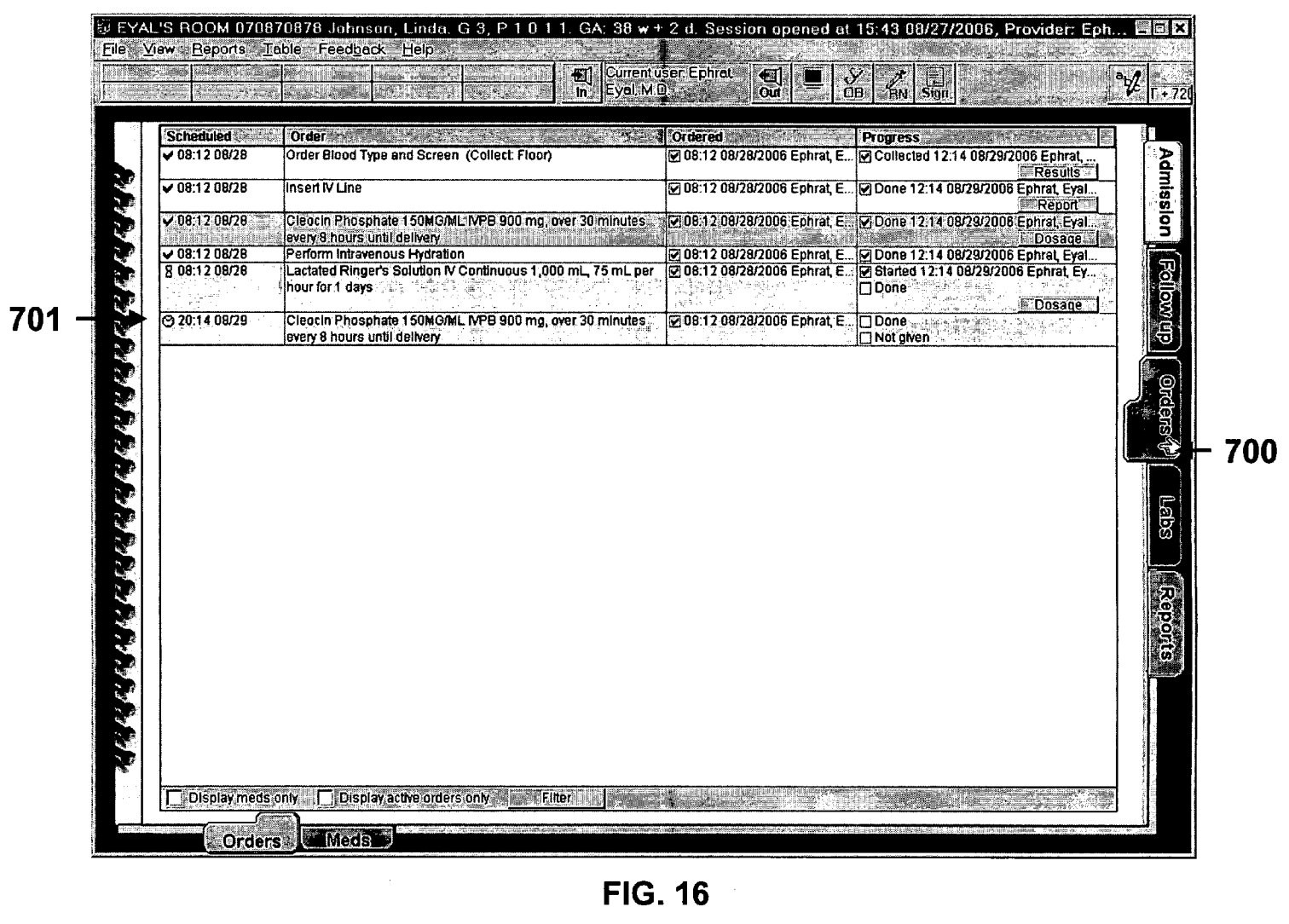

If a particular action or set of actions has not been completed by the scheduled time indicated in the schedule information column 207, the program 112 can generate reminder notifications alerting medical staff that an action or set of actions must still be completed. As illustrated in FIG. 16, a yellow finger 700 appears on the Orders tab, indicating there's an item that is overdue, as well as a yellow 701 that appears near the relevant overdue order. If the action or set of actions are not completed after a predetermined time, the program 112 can generate reminder notifications alerting medical staff that outstanding actions exist. The reminder notification can be displayed at the workstation 15 or the central terminal 17 at a predetermined time.

Figure 18A:
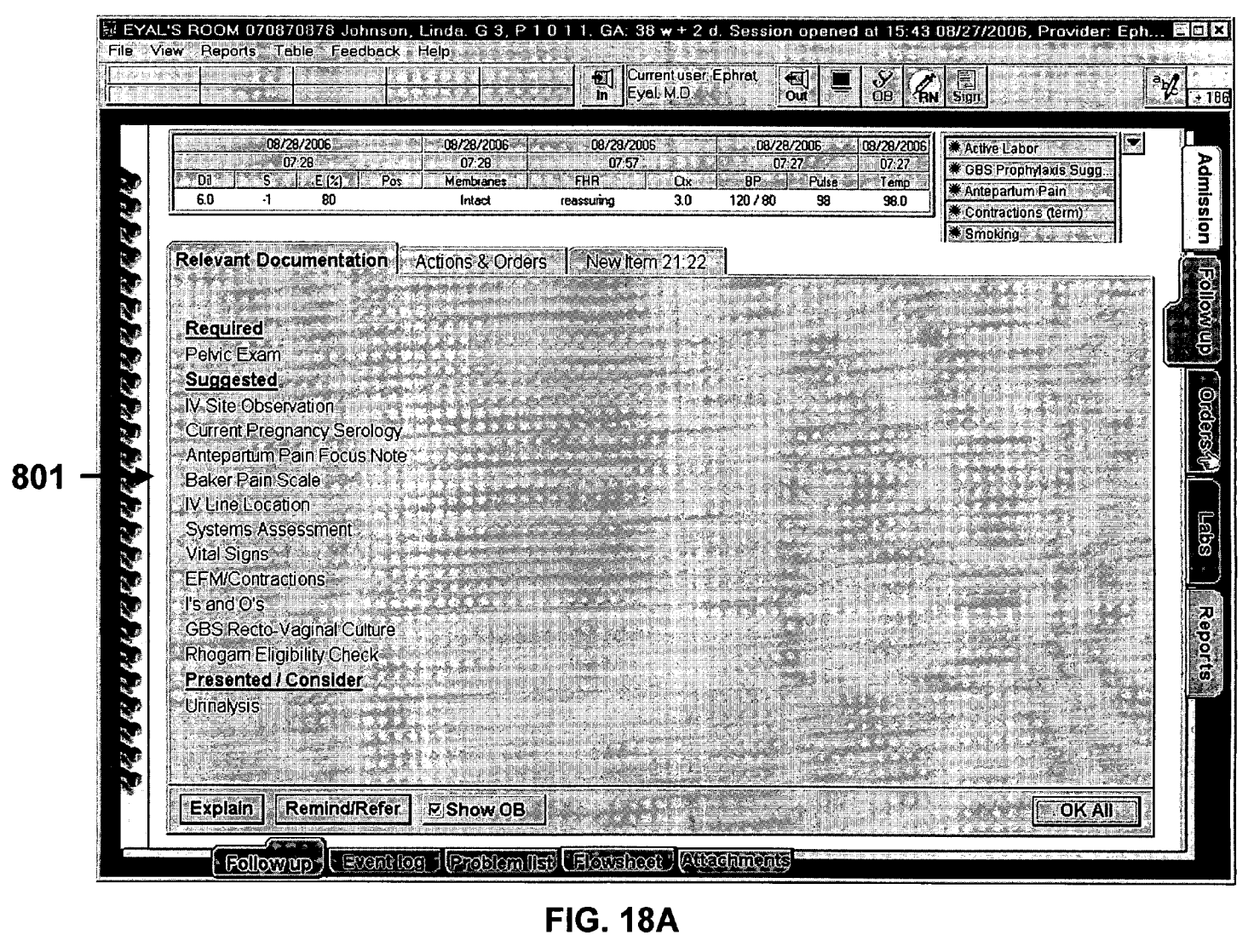
Figure 18B:
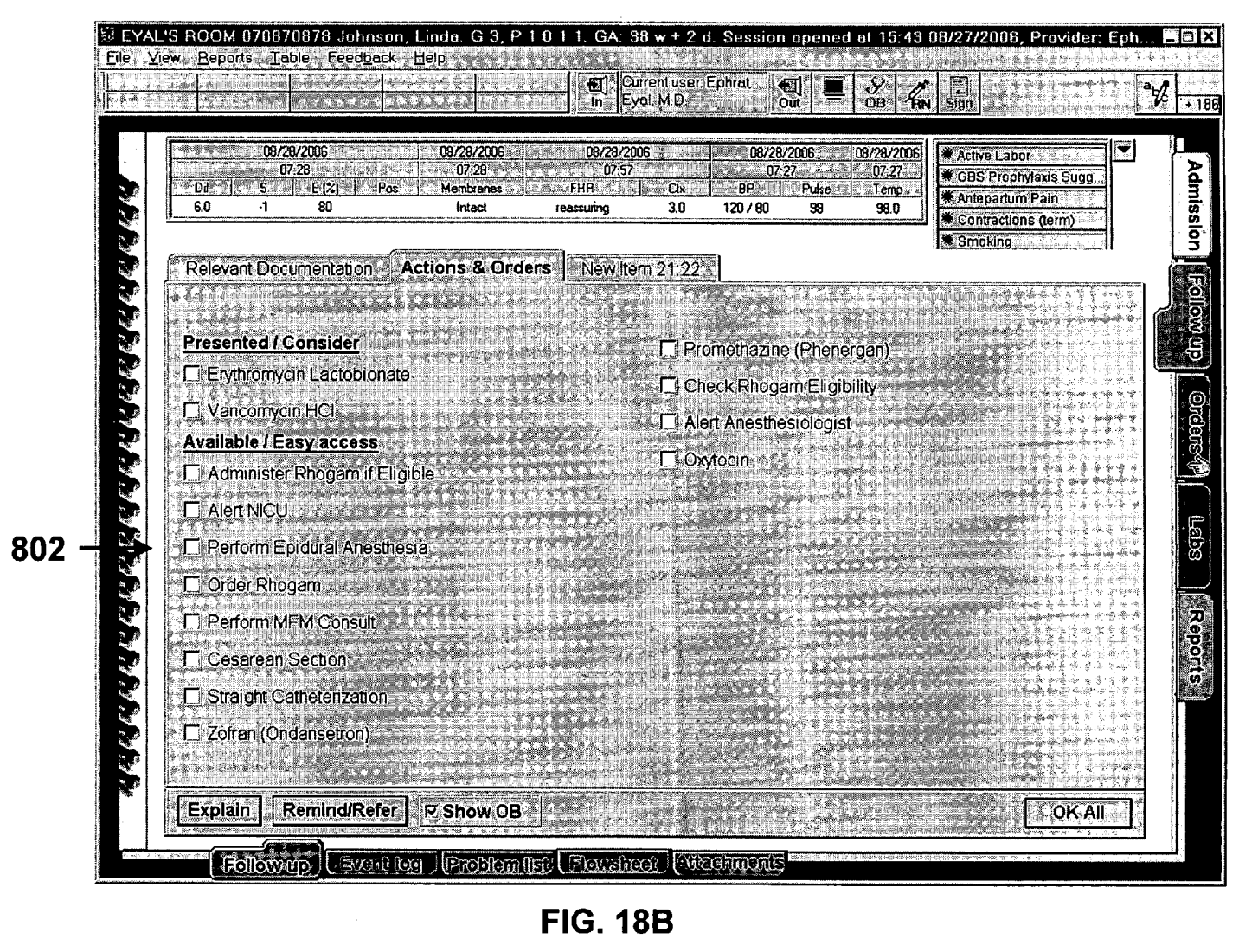

When the staff is not entering missing information, a decision, an action or a diagnosis that the system actively prompts for, and if that missing item is not critical for providing the appropriate patient care, the system will move this prompt to the New Item Section, as illustrated in FIGS. 18A and 18B. At any time during the patient care, the staff may click the New Item button 510, and be presented with the list of missing documentation or diagnosis items 801, as illustrated in FIG. 18A or with the list of missing Action items 802, as illustrated in FIG. 18B. This allows the staff to be reminded of missing items that were not dealt with when initially prompted and gain easy access to the items, instead of needing to search for them in the patient chart. Items that are critical for providing the appropriate patient care will be dealt by the system with the Compliance Adhering Mechanism, as previously discussed.

Figure 17A:
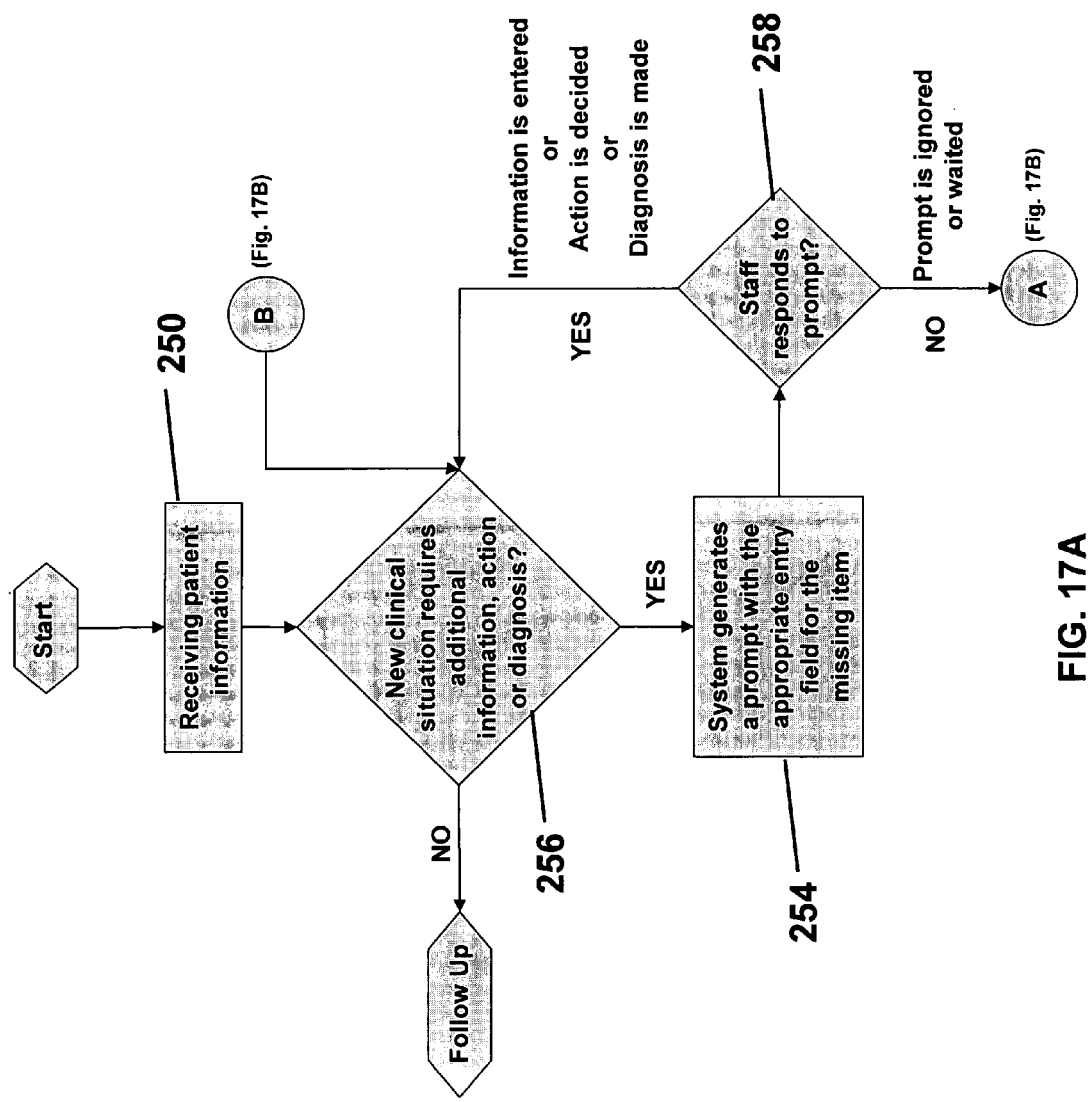
Figure 17B:
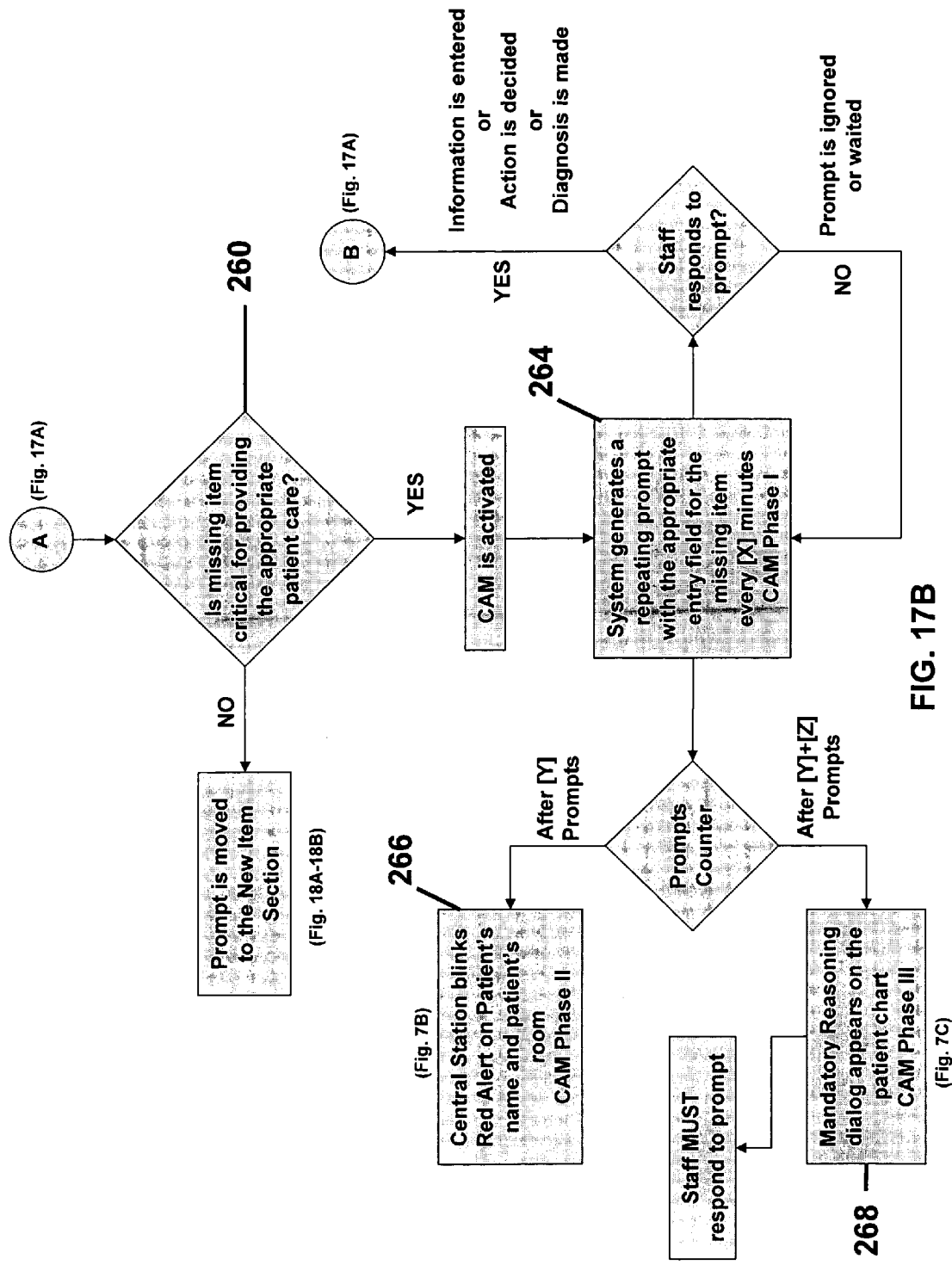

As noted, the methods described, and in particular the Compliance Adhering Mechanism method, are implemented with a computer program 112 comprising code segments for performing the various steps of these methods. With reference to FIG. 17A-17B, the process descriptions or blocks should be understood as representing modules, segments, or portions of code which include one or more executable instructions for implementing specific logical functions or steps in the process, and alternate implementations are included within the scope of the embodiments of the present invention in which functions may be executed out of order from that shown or discussed, including substantially concurrently or in reverse order, depending on the functionality involved, as would be understood by those having ordinary skill in the art.

The computer program comprises a plurality of software code segments. A code segment is provided for receiving at least one item of patient medical data 250. A code segment is provided for generating a first notification requesting at least one missing item 254 of patient medical information, diagnosis, action or decision. The notification is generated based on comparing 256 the at least one received item of patient medical data with a set of required items of patient medical data. A code segment is provided for displaying the first notification at a first predetermined time. The displayed first notification includes a selectable portion for inputting the at least one missing item of patient medical data. The computer program further comprises a code segment for determining if the at least one missing item of patient medical data has been received 258.

As seen in FIG. 17B, the system includes a code segment for determining if the missing item is critical for providing the appropriate clinical care 260. A code segment is provided to activate the CAM if the missing item is critical for providing the appropriate clinical care 262 and the system generates a repeating notification with the appropriate entry field for the missing item at a predetermined time interval until a staff member responds to the notification 264. The system provides a code segment for entering CAM Phase II after a predetermined time and generating a second notification at a central station 266, as describe previously. A code segment is provided for entering CAM Phase III after a predetermined time and generating a third notification 268. The third notification includes a mandatory reasoning prompt and requires the staff to respond to the notification.

While the foregoing has described what is considered to be the best mode and/or other examples, it is understood that various modifications may be made therein and that the subject matter disclosed herein may be implemented in various forms and examples, and that they may be applied in numerous other applications, combinations and environments, only some of which have been described herein. Those of ordinary skill in that art will recognize that the disclosed aspects may be altered or amended without departing from the true spirit and scope of the subject matter. Therefore, the subject matter is not limited to the specific details, exhibits and illustrated examples in this description. It is intended to protect any and all modifications and variations that fall within the true scope of the advantageous concepts disclosed herein.

I claim:

1. A non-transitory computer-readable storage medium storing instructions that, when executed by a processor, are configured to cause the processor to perform operations for providing real-time clinical decision support, the operations comprising:

receiving items of patient data;

comparing the received items of patient data with a set of best practice standards pertaining to an applicable clinical situation, the best practice standards including a plurality of best practice data items each associated with a criticality level;

identifying at least one best practice data item applicable to the clinical situation missing from the received items of patient data;

generating a request for the at least one missing item of patient data;

determining that the requested at least one missing item of patient data has not been received after a first time interval based on the criticality level of the at least one item of patient data;

generating a notification in a first compliance phase prompting for the at least one missing item of patient data, the notification configured to be dismissible and to return after a first time interval based on the criticality level of the at least one missing item of patient data, wherein the notification is configured to repeatedly return one or more times;

determining that the requested at least one missing item of patient data has not been received after a second time interval based on the criticality level of the at least one missing item of patient data;

generating an alert in a second compliance phase after the second time interval accentuating that the at least one missing item of patient data has not been received, wherein the alert is different than the notification in the first compliance phase;

determining that the requested at least one missing item of patient data has not been received after a third time interval based on the criticality level of the at least one missing item of patient data;

generating a request in a third compliance phase after the third time interval requesting an explanation for why the at least one missing item of patient data has not been received;

receiving a reason for why the missing item of patient data has not been received, instead of receiving the missing item of patient data; and dismissing the notification in the first compliance phase, the alert in the second compliance phase, and the request in the third compliance phase in response to receiving the reason for why the missing item of patient data has not been received.

2. The non-transitory computer-readable storage medium of claim 1 wherein the at least one missing item of patient data comprises at least one of patient information, a diagnosis, a decision, and an action to be taken.

3. The non-transitory computer-readable storage medium of claim 1 wherein the at least one missing item of patient data identifies one of at least whether a patient information has been received, whether a diagnosis has been diagnosed, whether a decision has been decided, and whether an action has been taken.

4. The non-transitory computer-readable storage medium of claim 1 wherein the notification is a visual notification that identifies the at least one item of patient data that has not been received.

5. The non-transitory computer-readable storage medium of claim 1 wherein the method further comprises displaying the first notification on at least one display.

6. The non-transitory computer-readable storage medium of claim 5 wherein the notification includes a selectable portion for entering data related to the at least one missing item of patient data.

7. The non-transitory computer-readable storage medium of claim 6 wherein the data related to the at least one missing item of patient data comprises either an indication that the at least one missing item of patient data will not be received or the at least one missing item of patient data.

8. The non-transitory computer-readable storage medium of claim 1, wherein at least two of the first time interval, the second time interval, and the third time interval are equal.

9. The non-transitory computer-readable storage medium of claim 1, wherein the notification is configured to return by being redisplayed on a display at predetermined time intervals, and
wherein the notification continues to be redisplayed until the at least one missing item of patient data is received or the reason for why the at least one missing item of patient data has not been received is received.

10. The non-transitory computer-readable storage medium of claim 1, wherein generating the alert comprises displaying the alert on at least one central location display, wherein the alert remains on the central location display until information corresponding to the at least one missing item of patient data is received or the reason for why the at least one missing item of patient data has not been received is received.

11. The non-transitory computer-readable storage medium of claim 1 wherein generating the request in the third compliance phase comprises displaying the request on a display, wherein the request remains on the display until data corresponding to the at least one missing item of data is received or the reason for why the at least one missing item of patient data has not been received is received.

12. The non-transitory computer-readable storage medium of claim 11 wherein the request comprises a selectable portion for entering data, and
wherein the selectable portion includes predetermined information corresponding to the at least one missing item of patient data that has not been received.

13. The non-transitory computer-readable storage medium of claim 1, wherein generating the alert in the second compliance phase comprises displaying the alert, wherein the alert remains on the display until data indicating that the uncompleted action is completed or the reason the at least one action has not been completed is entered.

14. The non-transitory computer-readable storage medium of claim 13 wherein the alert includes a selectable portion for indicating that the at least one action has been completed.

15. The non-transitory computer-readable storage medium of claim 13 wherein the operations further comprise generating a communication including a reason that the at least one action has not been completed.

16. A non-transitory computer-readable storage medium storing instructions that, when executed by a processor, are configured to cause the processor to perform operations, the operations comprising:
receiving items of completed actions;
determining at least one action required to be completed based on a set of best practice standards pertaining to an applicable clinical situation, the best practice standards including a plurality of data items;
determining if the at least one required action has been completed;
generating a first notification in a first compliance phase based on a determination that the at least one action has not been completed, the first notification configured to be dismissible and to return after a first time interval and identifying the at least one action that has not been completed and wherein the notification is configured to repeatedly return one or more times;
generating an alert in a second compliance phase based on a determination that the at least one action has not been completed after a second time interval, the alert accentuating that the at least one action has not been completed, wherein the alert is different than the notification in the first compliance phase;
generating a request in a third compliance phase based on a determination that the at least one action has not been completed after a third time interval requesting an explanation for why the at least one action has not been completed;
receiving a reason for why the at least one action has not been completed, instead of receiving the uncompleted action; and
dismissing the notification in the first compliance phase, the alert in the second compliance phase, and the request in the third compliance phase in response to receiving the reason for why the at least one action has not been completed.

17. The non-transitory computer-readable storage medium of claim 16 wherein the first notification includes a selectable portion for entering data corresponding to the at least one action that has not been completed.

18. The non-transitory computer-readable storage medium of claim 17 wherein the first notification includes a selectable portion for indicating that the at least one action has been completed.

19. The non-transitory computer-readable storage medium of claim 16 wherein the method further comprises:
receiving items of patient data;
comparing the received items of patient data with the set of best practice standards pertaining to an applicable clinical situation, the best practice standards including a plurality of data items; and
determining the at least one action required to be completed based in part on the comparison of the received items of patient data with the set of best practice rules standards.

20. The non-transitory computer-readable storage medium of claim 19 wherein the received items of patient data include at least one of one of patient information, diagnosis, decision, and action.

21. The non-transitory computer-readable storage medium of claim 19 wherein the method further comprises:
determining at least one suggested problem based on the comparison of the received items of patient data with the set of best practice standards;
displaying at least one suggested problem on a display, the at least one suggested problem being selectable; and
selecting the at least one suggested problem as at least one of a diagnosed problem, a suspected problem, and a non-existing problem.

22. The non-transitory computer-readable storage medium of claim 16 wherein the at least one action required to be completed is at least one of inputting additional items of patient data and performing at least a portion of a patient treatment procedure.

23. The non-transitory computer-readable storage medium of claim 16 wherein the method further comprises displaying the first notification on at least one display.

24. A non-transitory computer-readable storage medium storing instructions that, when executed by a processor, are configured to cause the processor to perform a method operations, the operations comprising:
receiving items of patient data;
comparing the received items of patient data with a set of best practice standards pertaining to an applicable clinical situation, the best practice standards including a plurality of best practice data items;

generating a first notification in a first compliance phase based on a determination that at least one item of patient data is missing that is included in the best practice data items for the applicable clinical situation;

displaying the first notification on a display, wherein the first notification includes a selectable portion for entering information corresponding to the at least one item of patient data that has not been received;

generating an alert in a second compliance phase after a second time interval accentuating that the at least one item of patient data has not been received, wherein the alert is different than the notification in the first compliance phase;

displaying the alert on the display, the alert configured to remain on the display until dismissed;

generating a request in a third compliance phase after a third time interval requesting an explanation for why the at least one missing item of patient data has not been received;

displaying the request on the display;

receiving a reason for why the missing item of patient data has not been received, instead of receiving the missing item of patient data; and dismissing the notification in the first compliance phase, the alert in the second compliance phase, and the request in the third compliance phase in response to receiving the reason for why the missing item of patient data has not been received.

25. The non-transitory computer-readable storage medium of claim 24 wherein the patient data includes at least one of patient information, diagnosis, decision, and action.

* * * * *